(12) United States Patent  (10) Patent No.: US 7,169,921 B2
Cheema et al.  (45) Date of Patent: Jan. 30, 2007

(54) PROCESS FOR THE PREPARATION OF OXABISPIDINES

(75) Inventors: Lal Cheema, Leicestershire (GB); David Cladingboel, Leicestershire (GB); Rhona Sinclair, Leichestershire (GB)

(73) Assignee: Astrazeneca AB, Sodertalje (SE)

( * ) Notice: Subject to any disclaimer, the term of this patent is extended or adjusted under 35 U.S.C. 154(b) by 271 days.

(21) Appl. No.: 10/474,593

(22) PCT Filed: Apr. 12, 2002

(86) PCT No.: PCT/SE02/00727

§ 371 (c)(1),
(2), (4) Date: Apr. 22, 2004

(87) PCT Pub. No.: WO02/083690

PCT Pub. Date: Oct. 24, 2002

(65) Prior Publication Data

US 2004/0181060 A1  Sep. 16, 2004

(30) Foreign Application Priority Data

Apr. 12, 2001  (SE)  .................................... 0101324

(51) Int. Cl.
*C07D 498/08* (2006.01)
(52) U.S. Cl. ........................................... 544/74; 560/9
(58) Field of Classification Search ................. 544/74; 560/9
See application file for complete search history.

(56) References Cited

U.S. PATENT DOCUMENTS 3,196,154 A  7/1965  Steck

FOREIGN PATENT DOCUMENTS

WO  WO-91/07405 A1  5/1991
WO  WO-01/28992 A2  4/2001

OTHER PUBLICATIONS

Barnes et al., "The Synthesis of the 3,9-Diazabicyclo [3.3.1] nonane Ring System," J. Am. Chem. Soc. 75:975-977 (1953).
Chapman et al., "Difluoramination of Heterocyclic Ketones: Control of Microbasicity," J. Org. Chem. 63:1566-1570 (1998).
Chapman et al., "Nitrolysis of a Highly Deactivated Amide by Protonitronium. Synthesis and Structure of HNFX," J. Org. Chem. 64:960-965 (1999).
Dave et al., "Facile Preparation of 3,7-Diazabicyclo[3,7-Diazabicyclo[3.3.0]octane and 3,7,10-Triheterocyclic [3.3.3]Propellane Ring Systems from 1,5-Diazacyclooctane 3,7-Derivatives," J. Org. Chem. 61:8897-8903 (1996).
Jeyaraman et al., "Chemistry of 3-Azabicyclo[3.3.1]nonanes," Chem. Rev. 81:149-174 (1981).

Kyi et al., "Synthetic Analgesics and Related Compounds. Part II Some Derivatives of 3:7-Diazabicyclo[3:3:1]nonane (Bispidine)," J. Med. Chem. Soc. pp. 1706-1708 (1951).
Paudler et al., "1,5-Bis(p-toluenesulfonyl)-3,7-Dihydroxyoctahydro-1,5-diazocine," J. Org. Chem. 31:277-280 (1966).
Paudler et al., "3,7-Disubstituted Octahydro-1,5-diazocines. Their Conversion into Tetrahydro-1,5-diazocines and into Ring-Contracted Products," J. Org. Chem. 32:2425-2430 (1967).
Rubtsov et al., "Synthesis and Pharmacological Investigation of Derivatives of 9-Methyl-3,9-diazabicyclo-(3,3,1)-nonane," Journal of Medicinal and Pharmaceutical Chemistry, 3(3):441-459 (1961).
Steck et al., "3-Substituted 9-Methyl-3,9-Diazabicyclo[3.3.1]nonanes," J. Org. Chem. 28(9):2233-2238 (1963).

*Primary Examiner*—Kahsay Habte
(74) *Attorney, Agent, or Firm*—Christer Hallgren; Cozen O'Connor, P.C.

(57) ABSTRACT

There is provided a process for the preparation of a compound of formula (I): which process comprises reaction of a compound of formula (II): with either a compound of formula (III): or acrylamide, followed, in the latter case, by reaction of the resulting intermediate of formula (IV): with an alcohol of formula $R^2$—OH and an agent that promotes, or agents that in combination promote, rearrangement and oxidation of the compound of formula IV to an intermediate isocyanate, which may then react with the alcohol of formula $R^2$—OH, and wherein $R^1$, $R^2$ and $R^{16}$ have meanings given in the description (I)

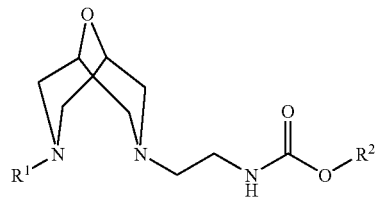

(II)

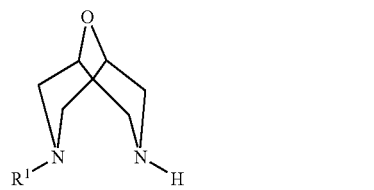

(III)

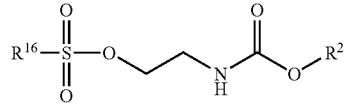

(IV)

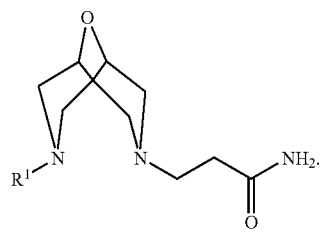

77 Claims, No Drawings

PROCESS FOR THE PREPARATION OF OXABISPIDINES

FIELD OF THE INVENTION

This invention relates to a novel process for the preparation of oxabispidine compounds that bear a N-2-(alkoxycarbonylamino)ethyl substituent.

PRIOR ART

The number of documented compounds including the 9-oxa-3,7-diazabicyclo-[3.3.1]nonane (oxabispidine) structure is very few. As a result, there are very few known processes that are specifically adapted for the preparation of oxabispidine compounds.

Certain oxabispidine compounds are disclosed in *Chem. Ber.* 96(11), 2827 (1963) as intermediates in the synthesis of 1,3-diaza-6-oxa-adamantanes.

Hemiacetals (and related compounds) having the oxabispidine ring structure are disclosed in *J. Org. Chem.* 31, 277 (1966), ibid. 61(25), 8897 (1996), ibid. 63(5), 1566 (1998) and ibid. 64(3), 960 (1999) as unexpected products from the oxidation of 1,5-diazacyclooctane-1,3-diols or the reduction of 1,5-diazacyclooctane-1,3-diones.

1,3-Dimethyl-3,7-ditosyl-9-oxa-3,7-diazabicyclo[3.3.1]nonane is disclosed in *J. Org. Chem.* 32, 2425 (1967) as a product from the attempted acetylation of trans-1,3-dimethyl-1,5-ditosyl-1,5-diazacyclooctane-1,3-diol.

None of the above-mentioned documents disclose or suggest the synthesis of oxabispidine compounds that bear a N-2-(alkoxycarbonylamino)ethyl substituent.

International patent application WO 01/28992 describes the synthesis of a wide range of oxabispidine compounds, which compounds are indicated as being useful in the treatment of cardiac arrhythmias. Amongst the compounds disclosed are a number that bear a N-2-(tert-butoxycarbonylamino)ethyl substituent. However, there is no disclosure in WO 01/28992 of processes for introducing N-2-(alkoxycarbonylamino)ethyl substituents into the oxabispidine nucleus that comprise either: (a) nucleophilic substitution of a sulfonate group from a 2-(alkoxycarbonylamino)ethyl sulfonate; or (b) reaction with acrylamide, followed by rearrangement of the resulting primary amide to an isocyanate intermediate, and subsequent reaction of that intermediate with an alcohol.

We have now found, surprisingly, that oxabispidine compounds that bear a N-2-(alkoxycarbonylamino)ethyl substituent may be prepared readily from the corresponding N-unsubstituted oxabispidines via such processes.

DESCRIPTION OF THE INVENTION

According to a first aspect of the invention there is provided a process for the preparation of a compound of formula I,

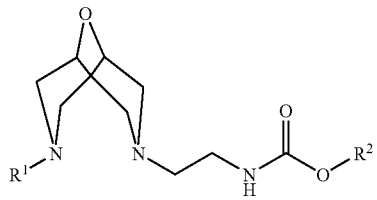

wherein $R^1$ represents H, an amino protective group or a structural fragment of formula Ia,

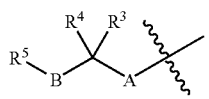

in which
$R^3$ represents H, halo, $C_{1-6}$ alkyl, —$OR^6$, -E-$N(R^7)R^8$ or, together with $R^4$, represents =O;
$R^4$ represents H, $C_{1-6}$ alkyl or, together with $R^3$, represents =O;
$R^6$ represents H, $C_{1-6}$ alkyl, -E-aryl, -E-Het$^1$, —$C(O)R^{9a}$, —$C(O)OR^{9b}$ or —$C(O)N(R^{10a})R^{10b}$;
$R^7$ represents H, $C_{1-6}$ alkyl, -E-aryl, -E-Het$^1$, —$C(O)R^{9a}$, —$C(O)OR^{9b}$, —$S(O)_2R^{9c}$, —$[C(O)]_pN(R^{10a})R^{10b}$ or —$C(NH)NH_2$;
$R^8$ represents H, $C_{1-6}$ alkyl, -E-aryl or —$C(O)R^{9d}$;
$R^{9a}$ to $R^{9d}$ independently represent, at each occurrence when used herein, $C_{1-6}$ alkyl (optionally substituted and/or terminated by one or more substituents selected from halo, aryl and Het$^2$), aryl, Het$^3$, or $R^{9a}$ and $R^{9d}$ independently represent H;
$R^{10a}$ and $R^{10b}$ independently represent, at each occurrence when used herein, H or $C_{1-6}$ alkyl (optionally substituted and/or terminated by one or more substituents selected from halo, aryl and Het$^4$), aryl, Het$^5$, or together represent $C_{3-6}$ alkylene, optionally interrupted by an O atom;
E represents, at each occurrence when used herein, a direct bond or $C_{1-4}$ alkylene;
p represents 1 or 2;
A represents -G-, -J-$N(R^{11})$— or -J-O— (in which latter two groups, $N(R^{11})$— or O— is attached to the carbon atom bearing $R^3$ and $R^4$);
B represents -Z-, -Z-$N(R^{12})$—, —$N(R^{12})$-Z-, -Z-$S(O)_n$— or -Z-O— (in which latter two groups, Z is attached to the carbon atom bearing $R^3$ and $R^4$);
G represents a direct bond or $C_{1-6}$ alkylene;
J represents $C_{2-6}$ alkylene;
Z represents a direct bond or $C_{1-4}$ alkylene;
$R^{11}$ and $R^{12}$ independently represent H or $C_{1-6}$ alkyl;
n represents 0, 1 or 2;
$R^5$ represents phenyl or pyridyl, both of which groups are optionally substituted by one or more substituents selected from —OH, cyano, halo, nitro, $C_{1-6}$ alkyl (optionally terminated by —$N(H)C(O)OR^{13a}$), $C_{1-6}$ alkoxy, —$N(R^{14a})R^{14b}$, —$C(O)R^{14c}$, —$C(O)OR^{14d}$, —$C(O)N$ $(R^{14e})R^{14f})N(R^{14g})C(R^{14h}$, —$N(R^{14i})C(O)N(R^{14j})R^{14k}$, —$N(R^{14m})S(O)_2R^{13b}$, —$S(O)_2R^{13c}$ and/or —$OS(O)_2R^{13d}$;

$R^{13a}$ to $R^{13d}$ independently represent $C_{1-6}$ alkyl;

$R^{14a}$ and $R^{14b}$ independently represent H, $C_{1-6}$ alkyl or together represent $C_{3-6}$ alkylene, resulting in a four- to seven-membered nitrogen-containing ring;

$R^{14c}$ to $R^{14m}$ independently represent H or $C_{1-6}$ alkyl; and

Het$^1$ to Het$^5$ independently represent, at each occurrence when used herein, five- to twelve-membered heterocyclic groups containing one or more heteroatoms selected from oxygen, nitrogen and/or sulfur, which heterocyclic groups are optionally substituted by one or more substituents selected from =O, —OH, cyano, halo, nitro, $C_{1-6}$ alkyl, $C_{1-6}$ alkoxy, aryl, aryloxy, —$N(R^{15a})R^{15b}$, —$C(O)R^{15c}$, —$C(O)OR^{15d}$, —$C(O)N(R^{15e})R^{15f}$, —$N(R^{15g})C(O)R^{15h}$ and —$N(R^{15i})S(O)_2R^{15j}$;

$R^{15a}$ to $R^{15j}$ independently represent $C_{1-6}$ alkyl, aryl or $R^{15a}$ to $R^{15i}$ independently represent H;

provided that:

(a) when $R^4$ represents H or $C_{1-4}$ alkyl; and
A represents -J-N(R$^{11}$)— or -J-O—;
then B does not represent —N(R$^{12}$)—, —S(O)$_n$—, —O— or —N(R$^{12}$)-Z- (in which latter group —N(R$^{12}$) is attached to the carbon atom bearing R$^3$ and R$^4$);

(b) when R$^3$ represents —OR$^6$ or -E-N(R$^7$)R$^8$ in which E represents a direct bond, then:
(i) A does not represent a direct bond, -J-N(R$^{11}$)— or -J-O—; and
(ii) B does not represent —N(R$^{12}$)—, —S(O)$_n$—, —O— or —N(R$^{12}$)-Z- (in which latter group —N(R$^{12}$) is attached to the carbon atom bearing R$^3$ and R$^4$); and R$^2$ represents $C_{1-6}$ alkyl (optionally substituted and/or terminated by one or more substituents selected from —OH, halo, cyano, nitro and aryl) or aryl, wherein each aryl and aryloxy group, unless otherwise specified, is optionally substituted;

which process comprises reaction of a compound of formula II,

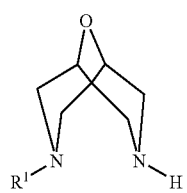

II wherein R$^1$ is as defined above, with either:
(i) a compound of formula III,

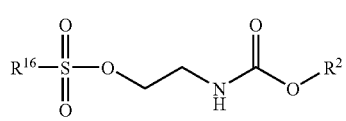

III wherein R$^{16}$ represents unsubstituted $C_{1-4}$ alkyl, $C_{1-4}$ perfluoroalkyl or phenyl, which latter group is optionally substituted by one or more substituents selected from $C_{1-6}$ alkyl, halo, nitro and $C_{1-6}$ alkoxy, and R$^2$ is as defined above; or (ii) acrylamide, followed by reaction of the resulting intermediate of formula IV,

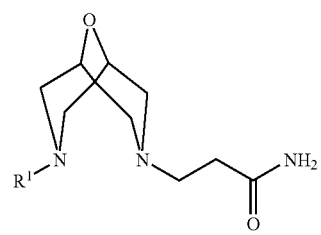

IV wherein R$^1$ is as defined above, with an alcohol of formula R$^2$—OH and an agent that promotes, or agents that in combination promote, rearrangement and oxidation of the compound of formula IV to an intermediate isocyanate, which may then react with the alcohol of formula R$^2$—OH, wherein R$^2$ is as defined above, and which process is referred to hereinafter as "the process of the invention".

Unless otherwise specified, alkyl groups and alkoxy groups as defined herein may be straight-chain, or, when there is a sufficient number (i.e. a minimum of three) of carbon atoms be branched-chain, and/or cyclic. Further, when there is a sufficient number (i.e. a minimum of four) of carbon atoms, such alkyl and alkoxy groups may also be part cyclic/acyclic. Such alkyl and alkoxy groups may also be saturated or, when there is a sufficient number (i.e. a minimum of two) of carbon atoms, be unsaturated and/or interrupted by one or more oxygen and/or sulfur atoms. Unless otherwise specified, alkyl and alkoxy groups may also be substituted by one or more halo, and especially fluoro, atoms.

Unless otherwise specified, alkylene groups as defined herein may be straight-chain or, when there is a sufficient number (i.e. a minimum of two) of carbon atoms, be branched-chain. Such alkylene chains may also be saturated or, when there is a sufficient number (i.e. a minimum of two) of carbon atoms, be unsaturated and/or interrupted by one or more oxygen and/or sulfur atoms. Unless otherwise specified, alkylene groups may also be substituted by one or more halo atoms.

The term "aryl", when used herein, includes $C_{6-10}$ aryl groups such as phenyl, naphthyl and the like. The term "aryloxy", when used herein includes $C_{6-10}$ aryloxy groups such as phenoxy, naphthoxy and the like. For the avoidance of doubt, aryloxy groups referred to herein are attached to the rest of the molecule via the O-atom of the oxy-group. Unless otherwise specified, aryl and aryloxy groups may be substituted by one or more substituents including —OH, cyano, halo, nitro, $C_{1-6}$ alkyl, $C_{1-6}$ alkoxy, —N(R$^{14a}$)R$^{14b}$, —C(O)R$^{14c}$, —C(O)OR$^{14d}$, —C(O)N(R$^{14e}$)R$^{14f}$, —N(R$^{14g}$)C(O)R$^{14h}$, —N(R$^{14m}$)S(O)$_2$R$^{13b}$, —S(O)$_2$R$^{13c}$ and/or —OS(O)$_2$R$^{13d}$ (wherein R$^{13b}$ to R$^{13d}$ and R$^{14a}$ to R$^{14m}$ are as hereinbefore defined). When substituted, aryl and aryloxy groups are preferably substituted by between one and three substitutents.

The term "halo", when used herein, includes fluoro, chloro, bromo and iodo.

Het (Het$^1$ to Het$^5$) groups that may be mentioned include those containing 1 to 4 heteroatoms (selected from the group oxygen, nitrogen and/or sulfur) and in which the total number of atoms in the ring system are between five and twelve. Het (Het$^1$ to Het$^5$) groups may be fully saturated, wholly aromatic, partly aromatic and/or bicyclic in character. Heterocyclic groups that may be mentioned include benzodioxanyl, benzodioxepanyl, benzodioxolyl, benzofuranyl, benzimidazolyl, benzomorpholinyl, benzoxazinonyl, benzothiophenyl, chromanyl, cinnolinyl, dioxanyl, furanyl, imidazolyl, imidazo[1,2-a]pyridinyl, indolyl, isoquinolinyl, isoxazolyl, morpholinyl, oxazolyl, phthalazinyl, piperazinyl, piperidinyl, purinyl, pyranyl, pyrazinyl, pyrazolyl, pyridinyl, pyrimindinyl, pyrrolidinonyl, pyrrolidinyl, pyrrolinyl, pyrrolyl, quinazolinyl, quinolinyl, tetrahydropyranyl, tetrahydrofuranyl, thiazolyl, thienyl, thiochromanyl, triazolyl and the like. Substituents on Het (Het$^1$ to Het$^5$) groups may, where appropriate, be located on any atom in the ring system including a heteroatom. The point of attachment of Het (Het$^1$ to Het$^5$) groups may be via any atom in the ring system including (where appropriate) a heteroatom, or an atom on any fused carbocyclic ring that may be present as part of the ring system. Het (Het$^1$ to Het$^5$) groups may also be in the N- or S-oxidised form.

As used herein, the term "amino protective group" includes groups mentioned in "Protective Groups in Organic Synthesis", 2$^{nd}$ edition, T W Greene & P G M Wutz, Wiley-Interscience (1991), in particular those indexed at the start of the chapter entitled "Protection for the Amino Group" (see pages 309 to 315) of that reference, the disclosure in which document is hereby incorporated by reference.

Specific examples of amino protective groups thus include:

(a) those which form carbamate groups (e.g. to provide methyl, cyclopropylmethyl, 1-methyl-1-cyclopropylmethyl, diisopropylmethyl, 9-fluorenylmethyl, 9-(2-sulfo)fluorenylmethyl, 2-furanylmethyl, 2,2,2-trichloroethyl, 2-haloethyl, 2-trimethylsilylethyl, 2-methylthioethyl, 2-methylsulfonylethyl, 2(p-toluenesulfonyl)ethyl, 2-phosphonioethyl, 1,1-dimethylpropynyl, 1,1-dimethyl-3-(N,N-dimethylcarboxamido)-propyl, 1,1-dimethyl-3-(N,N-dietbylamino)propyl, 1-methyl-1-(1-adamantyl)ethyl, 1-methyl-1-phenylethyl, 1-methyl-1-(3,5-dimethoxyphenyl)ethyl, 1-methyl-1-(4-biphenylyl)ethyl, 1-methyl-1-(p-phenylazophenyl)ethyl, 1,1-dimethyl-2-haloethyl, 1,1-dimethyl-2,2,2-trichloroethyl, 1,1-dimethyl-2-cyanoethyl, isobutyl, t-butyl, t-amyl, cyclobutyl, 1-methylcyclobutyl, cyclopentyl, cyclohexyl, 1-methylcyclohexyl, 1-adamantyl, isobornyl, vinyl, allyl, cinnamyl, phenyl, 2,4,6-tri-t-butylphenyl, m-nitrophenyl, S-phenyl, 8-quinolinyl, N-hydroxypiperidinyl, 4-(1,4-dimethylpiperidinyl), 4,5-diphenyl-3-oxazolin-2-one, benzyl, 2,4,6-trimethylbenzyl, p-methoxybenzyl, 3,5-dimethoxybenzyl, p-decyloxybenzyl, p-nitrobenzyl, o-nitrobenzyl, 3,4-dimethoxy-6-nitrobenzyl, p-bromobenzyl, chlorobenzyl, 2,4-dichloro-benzyl, p-cyanobenzyl, o-(N,N-dimethylcarboxamidobenzyl)benzyl, m-chloro-p-acyloxybenzyl, p-(dihydroxyboryl) benzyl, p-(phenylazo)benzyl, p-(p'-methoxyphenylazo) benzyl, 5-benzisoxazolylmethyl, 9-anthrylmethyl, diphenylmethyl, phenyl(o-nitrophenyl)methyl, di(2-pyridyl)methyl, 1-methyl-1-(4-pyridyl)-ethyl, isonicotinyl, or S-benzyl, carbamate groups);

(b) those which form amide groups (e.g. to provide N-formyl, N-acetyl, N-chloroacetyl, N-dichloro-acetyl, N-trichloroacetyl, N-trifluoroacetyl, N-o-nitrophenylacetyl, N-o-nitrophenoxyacetyl, N-acetoacetyl, N-acetylpyridinium, N-3-phenylpropionyl, N-3-(p-hydroxyphenyl)propionyl, N-3-(o-nitro-phenyl)propionyl, N-2-methyl-2-(o-nitro-phenoxy)propionyl, N-2-methyl-2-(o-phenylazophenoxy)propionyl, N-4-chlorobutyryl, N-isobutyryl, N-o-nitrocinnamoyl, N-picolinoyl, N-(N'-acetyl-methionyl), N-(N'-benzoylphenylalanyl), N-benzoyl, N-p-phenyl-benzoyl, N-p-methoxybenzoyl, N-o-nitrobenzoyl, or N-o-(benzoyloxy-methyl)benzoyl, amide groups);

(c) those which form N-alkyl groups (e.g. N-allyl, N-phenacyl, N-3-acetoxypropyl, N-(4-nitro-1-cyclohexyl-2-oxo-pyrrolin-3-yl), N-methoxymethyl, N-chloroethoxymethyl, N-benzyloxymethyl, N-pivaloyloxymethyl, N-2-tetrahydropyranyl, N-2,4-dinitrophenyl, N-benzyl, N-3,4-di-methoxybenzyl, N-o-nitrobenzyl, N-di(p-methoxyphenyl)methyl, N-triphenylmethyl, N-(p-methoxyphenyl)-diphenylmethyl, N-diphenyl-4-pyridylmethyl, N-2-picolyl N'-oxide, or N-dibenzosuberyl, groups);

(d) those which form N-phosphinyl and N-phosphoryl groups (e.g. N-diphenylphosphinyl, N-dimethylthiophosphinyl, N-diphenylthiophosphinyl, N-diethylphosphoryl, N-dibenzylphosphoryl, or N-phenylphosphoryl, groups);

(e) those which form N-sulfenyl groups (e.g. N-benzenesulfenyl, N-o-nitrobenzenesulfenyl, N-2,4-dinitrobenzenesulfenyl, N-pentachlorobenzenesulfenyl, N-2-nitro-4-methoxybenzenesulfenyl, or N-triphenylmethylsulfenyl, groups);

(f) those which form N-sulfonyl groups (e.g. N-benzenesulfonyl, N-p-nitrobenzenesulfonyl, N-p-methoxybenzenesulfonyl, N-2,4,6-trimethylbenzene-sulfonyl, N-toluenesulfonyl, N-benzylsulfonyl, N-p-methylbenzyl-sulfonyl, N-trifluoromethylsulfonyl, or N-phenacylsulfonyl, groups); and (g) that which forms the N-trimethylsilyl group.

Preferred amino protective groups include those which provide the carbamate, N-alkyl and N-sulfonyl groups mentioned above. Particular protecting groups thus include tert-butoxycarbonyl (to form a tert-butylcarbamate group), benzenesulfonyl, 4-nitrobenzenesulfonyl, 3,4-dimethoxybenzyl, o-nitrobenzyl and, especially, benzyl groups.

The skilled person will appreciate that the conversion of the intermediate of formula IV to the compound of formula I is a transformation that is akin to a classical "Hofmann" rearrangement, except that, in the process of the invention, the intermediate isocyanate compound is "trapped" with an alcohol of formula R$^2$OH, as opposed to water. In this respect, agents that may be used to effect the rearrangement/ oxidation process include combinations of halogenating agents and bases, such as a combination of a brominating agent and a base. Suitable halogenating agents include any source of "electrophilic" halogen (e.g. N-halosuccinimides and halogens).

Other agents that may be used to effect the above-mentioned rearrangement include Pb(OAc)$_4$.

Preferred values of R$^1$ include an amino protective group, or a structural fragment of formula Ia in which:

R$^3$ represents H, halo, C$_{1-3}$ alkyl, —OR$^6$, —N(H)R$^7$ or, together with R$^4$, represents =O;

R$^4$ represents H, C$_{1-3}$ alkyl or, together with R$^3$, represents =O;

R$^6$ represents H, C$_{1-6}$ alkyl, -E-phenyl (which phenyl group is optionally substituted by one or more substituents selected from cyano, halo, nitro, C$_{1-4}$ alkyl and C$_{1-4}$ alkoxy) or -E-Het$^1$;

R$^7$ represents H, C$_{1-6}$ alkyl, -E-phenyl (which phenyl group is optionally substituted by one or more substituents selected from cyano, halo, nitro, $C_{1-4}$ alkyl and $C_{1-4}$ alkoxy), —C(O)$R^{9a}$, —C(O)O$R^{9b}$, —S(O)$_2R^{9c}$, —C(O)N($R^{10a}$)$R^{10b}$ or —C(NH)NH$_2$;

$R^{9a}$ to $R^{9c}$ independently represent $C_{1-6}$ alkyl, or $R^{9a}$ represents H;

$R^{10a}$ and $R^{10b}$ independently represent H or $C_{1-4}$ alkyl;

E represents, at each occurrence when used herein, a direct bond or $C_{1-2}$ alkylene;

A represents -G-, -J-N($R^{11}$)— or -J-O— (in which latter two groups, N($R^{11}$)— or O— is attached to the carbon atom bearing $R^3$ and $R^4$);

B represents -Z-, -Z-N($R^{12}$)—, -Z-S(O)$_n$— or -Z-O—;

G represents $C_{1-4}$ alkylene;

J represents $C_{2-4}$ alkylene;

Z represents a direct bond or $C_{1-3}$ alkylene;

$R^{11}$ and $R^{12}$ independently represent H or $C_{1-4}$ alkyl;

n represents 0 or 2;

$R^5$ represents phenyl or pyridyl, both of which groups are optionally substituted by one or more substituents selected from cyano, halo, nitro, $C_{1-6}$ alkyl, $C_{1-6}$ alkoxy, —NH$_2$, —C(O)N($R^{14e}$)$R^{14f}$, —N($R^{14g}$)C(O)$R^{14h}$ and —N($R^{14m}$)S(O)$_2R^{13b}$;

$R^{13b}$ represents $C_{1-3}$ alkyl;

$R^{14e}$ to $R^{14m}$ independently represent, at each occurrence when used herein, H or $C_{1-4}$ alkyl;

Het$^1$ to Het$^5$ are optionally substituted by one or more substituents selected from =O, cyano, halo, nitro, $C_{1-4}$ alkyl, $C_{1-4}$ alkoxy, —N($R^{15a}$)$R^{15b}$, —C(O)$R^{15c}$, or —C(O)O$R^{15d}$;

$R^{15a}$ to $R^{15d}$ independently represent H, $C_{1-4}$ alkyl or aryl.

Values of $R^1$ that are more preferred include an amino protective group, or a structural fragment of formula Ia in which:

$R^3$ represents H, methyl, —OR$^6$ or —N(H)R$^7$;

$R^4$ represents H or methyl;

$R^6$ represents H, $C_{1-2}$ alkyl or phenyl (which phenyl group is optionally substituted by one or more substituents selected from cyano and $C_{1-4}$ alkoxy);

$R^7$ represents H, $C_{1-2}$ alkyl, phenyl (which phenyl group is optionally substituted by one or more substituents selected from cyano, halo, nitro, $C_{1-4}$ alkyl and $C_{1-4}$ alkoxy), —C(O)$R^{9a}$ or —C(O)O$R^{9b}$;

$R^{9a}$ and $R^{9b}$ independently represent $C_{1-6}$ alkyl;

A represents $C_{1-4}$ alkylene;

B represents -Z-, -Z-N($R^{12}$)—, -Z-S(O)$_2$— or -Z-O—;

$R^{12}$ represents H or methyl;

$R^5$ represents pyridyl or phenyl, which latter group is optionally substituted by one to three substituents selected from cyano, nitro, $C_{1-2}$ alkoxy, NH$_2$ and —N(H)S(O)$_2$CH$_3$.

Values of $R^1$ that are more preferred still include an amino protective group, or a structural fragment of formula Ia in which:

$R^3$ represents H, —OR$^6$ or —N(H)R$^7$;

$R^6$ represents H or phenyl (optionally substituted by one or more substituents selected from cyano and $C_{1-2}$ alkoxy);

$R^7$ represents H, phenyl (optionally substituted by one or more cyano groups) or —C(O)O—$C_{1-5}$ alkyl;

A represents $C_{1-3}$ alkylene;

B represents -Z-, -Z-N(H)—, -Z-S(O)$_2$— or -Z-O—;

$R^5$ represents phenyl substituted by cyano in the ortho- and/or, in particular, the para-position relative to B.

Particularly preferred values of $R^1$ include an amino protective group, or a structural fragment of formula Ia in which:

$R^3$ represents H or —OH;

$R^4$ represents H;

A represents CH$_2$;

B represents -Z-, -Z-N(H)— or -Z-O—;

Z represents a direct bond or $C_{1-2}$ alkylene;

$R^5$ represents para-cyanophenyl.

Especially preferred values of $R^1$ include an amino protective group, or the following sub-structures

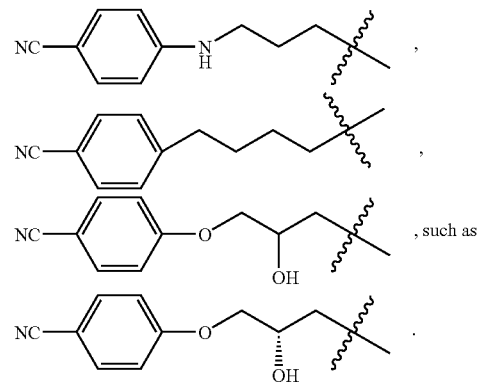

, such as

The process of the invention is most preferably carried out to provide compounds of formula I in which $R^1$ is an amino protective group as defined above, such as benzyl.

Preferred values of $R^2$ include $C_{1-6}$ alkyl, particularly saturated $C_{1-6}$ alkyl.

More preferred values of $R^2$ include saturated $C_{3-5}$ alkyl, particularly saturated $C_4$ alkyl, such as tert-butyl.

Preferred values of $R^{16}$ include phenyl, optionally substituted by one or more (e.g. one to three) substituents (e.g. one substituent) selected from $C_{1-3}$ alkyl (e.g. methyl), halo and nitro, particularly unsubstituted phenyl, methylphenyl (such as 4-methylphenyl) or trimethylphenyl (such as 2,4,6-trimethylphenyl).

The process of the invention is preferably carried out in the presence of a suitable solvent system. This solvent system should not give rise to stereochemical changes in the reactants or product once formed.

For reaction between compounds of formula II and compounds of formula III, the following may be the case.

(a) Suitable solvents include water and organic solvents. Preferred solvents include DMF, N-methylpyrrolidinone, dichloromethane, acetonitrile, DMSO, lower alkyl (e.g. $C_{1-6}$ alkyl) alcohols (such as ethanol), lower alkyl (e.g. $C_{1-6}$ alkyl) esters (e.g. $C_{1-6}$ alkyl acetates (such as iso-propyl acetate)), water, aromatic hydrocarbons (such as toluene) or mixtures thereof. Particularly preferred solvents include iso-propyl acetate, water, toluene and mixtures thereof.

(b) Reaction may be carried out in the presence of a base. In this respect, suitable bases include tertiary amines such as tri($C_{1-6}$ alkyl)amines (e.g. triethylamine), alkali metal carbonates and alkali metal hydrogencarbonates and alkali metal hydroxides. Preferred bases include alkali metal hydrogencarbonates, such as sodium hydrogencarbonate, and alkali metal hydroxides, such as sodium hydroxide.

(c) Reaction is preferably carried out at, or above, ambient temperature (e.g. between 10 and 100° C., preferably between 15 and 85° C., and, particularly, between 20 and 75° C.). For example, where the solvent system that is employed is a mixture of water and toluene, the reaction may be carried out at between 55 and 75° C. (such as between 65 and 70° C.). Where the solvent system is toluene (alone), the reaction may be carried out at between 60 and 70° C.

(d) The stoichiometric ratio of the compound of formula II to the compound of formula III is preferably within the range of 3:2 to 2:3, particularly within the range 5:4 to 8:11 (such as within the range 11:10 to 5:6), and, especially, within the range 1:1 to 10:11, such as 1:1.

(e) Reaction may, if appropriate be followed by isolation of the appropriate sulfonic acid salt. We have found advantageously that where reaction takes place between a compound of formula II in which $R^1$ is an amino protective group, such as benzyl, and a compound of formula III in which $R^2$ represents tert-butyl and $R^{16}$ represents 2,4,6-trimethylphenyl, the resultant sulfonic acid salt may be readily isolated in high purity by way of simple filtration, particularly when the compounds of formulae II and III are reacted together by heating in the presence of an aromatic hydrocarbon, such as toluene as solvent.

(f) Irrespective of whether the sulfonic acid salt is isolated, reaction may be followed by neutralisation of that salt under appropriate conditions, such as those described hereinafter.

For reaction between compounds of formula II and acrylamide, the following may be the case.

(A) Suitable solvents include polar solvents such as DMF, N-methyl-pyrrolidinone, acetonitrile, DMSO, lower alkyl (e.g. $C_{1-6}$ alkyl) alcohols (such as ethanol), water, and mixtures thereof. Preferred solvents include $C_{1-1}$ alkyl alcohols such as ethanol.

(B) Reaction is preferably carried out in the absence of base, although a suitable base (such as a tertiary amine (e.g. triethylamine)) may be employed where the compound of formula II is provided as an acid addition salt.

(C) Reaction is preferably carried out at above ambient temperature, such as between room and reflux temperature of the solvent employed (e.g. between 25 and 100° C., preferably between 45 and 90° C., and, particularly, between 60 and 85° C.). For example, where the solvent system that is employed is ethanol, the reaction may be carried out at around reflux temperature (such as between 65 and 80° C., and, particularly, between 70 and 80° C.).

(D) The stoichiometric ratio of the compound of formula II to acrylamide is preferably within the range of 3:2 to 2:3, particularly within the range 5:4 to 8:11 (such as within the range 11:10 to 5:6), and, especially, within the range 1:1 to 10:11 (such as within the range 1:1 to 20:21.

(E) The intermediate compound of formula IV that is formed may be purified by conventional techniques, such as recrystallisation. Suitable solvents for such a recrystallisation procedure include $C_{3-8}$ alkyl esters (such as n-propyl acetate, iso-propyl acetate and, particularly, ethyl acetate).

When the intermediate formed by reaction between compounds of formula II and acrylamide (the compound of formula IV) is reacted with a brominating agent, base and the alcohol of formula $R^2$—OH, the following may be the case.

(i) Reaction is optionally carried out in the presence of a suitable solvent system. However, it is preferred that the alcohol $R^2$—OH is present in excess such that it may act both as a reagent and as a solvent for the compound of formula IV.

(ii) Suitable brominating agents include any source of 'electrophilic' bromine, and thus include bromine and N-bromoimido compounds. Preferred brominating agents include N-bromosuccinimide.

(iii) Suitable bases include alkali metal hydroxides and alkoxides. Preferred bases include alkali metal $C_{1-6}$ alkoxides, such as potassium $C_{3-5}$ alkoxides (e.g. potassium tert-butoxide).

(iv) Reaction is preferably carried out at above ambient temperature, such as between room and reflux temperature of the solvent employed (e.g. between 25 and 100° C., preferably between 45 and 90° C. and, particularly, between 55 and 80° C.). For example, when the alcohol is tert-butanol, the reaction may be carried out at between 55 and 70° C., preferably between 57 and 67° C. and, particularly, between 60 and 65° C.

(v) The stoichiometric ratio of the compound of formula IV to the brominating agent is preferably within the range 1:1 to 1:7, particularly within the range 2:3 to 1:5 (such as within the range 1:2 to 1:3) and, especially, within the range 2:5 to 7:20.

(vi) The stoichiometric ratio of the compound of formula IV to the base is preferably within the range 1:1 to 1:20, particularly within the range 1:2 to 1:10 (such as within the range 1:3 to 2:15) and, especially, within the range 5:27 to 1:7.

Compounds of formula II may be prepared as described in international patent application WO 01/28992.

For example compounds of formula II may be prepared by dehydrative cyclisation of a corresponding compound of formula V,

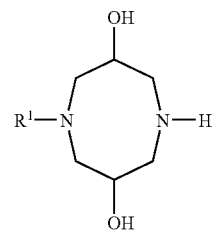

or a protected (e.g. N-benzenesulfonyl or N-nitrobenzenesulfonyl (e.g. N-4-nitrobenzenesulfonyl) derivative thereof, wherein $R^1$ is as hereinbefore defined. This cyclisation may be carried out, for example in the presence of a suitable dehydrating agent (such as: a strong acid (e.g. sulfuric acid (e.g. concentrated sulfuric acid) or, particularly, methanesulfonic acid (especially anhydrous methanesulfonic acid) and the like); an acid anhydride such as acetic anhydride or trifluoromethane-sulfonic anhydride; $P_2O_5$ in methanesulfonic acid; a phosphorous-based halogenating agent such as $P(O)Cl_3$, $PCl_3$ or $PCl_5$; or thionyl chloride). The cyclisation may also be carried out in the presence of a suitable organic solvent system, which solvent system should not significantly react chemically with, or significantly give rise to stereochemical changes in, the reactant or product once formed, or significantly give rise to other side reactions. Preferred solvent systems include aromatic solvents (e.g. an aromatic hydrocarbon, such as toluene or xylene, or a chlorinated aromatic hydrocarbon, such as chlorobenzene or dichlorobenzene), or dichloroethane, optionally in the presence of further solvents such as ethanol and/or ethyl acetate. When the dehydrating agent is methanesulfonic acid, preferred solvent systems include toluene. When the dehydrating agent is sulfuric acid, preferred solvent systems include chlorobenzene or no solvent. The cyclisation may be carried out at elevated temperature (e.g. up to the reflux temperature of the relevant solvent system, or higher if a pressurised system is employed). Clearly, appropriate reaction times and reaction temperatures depend upon the solvent system that is employed, as well as the reactants that are used and the compound that is to be formed, but these may be determined routinely by the skilled person.

Compounds of formula II in which $R^1$ represents H or an amino protective group may alternatively be prepared according to, or by analogy with, known techniques, such as reaction of a compound of formula VI,

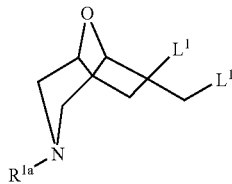

VI wherein $R^{1a}$ represents H or an amino protective group (as hereinbefore defined) and $L^1$ represents a suitable leaving group (e.g. halo, such as iodo), with ammonia or a protected derivative thereof (e.g. benzylamine), for example under conditions such as those described in Chem. Ber. 96(11), 2827 (1963).

Compounds of formula II in which $R^1$ represents a structural fragment of formula Ia may alternatively be prepared by reaction of the compound of formula II in which $R^1$ represents H (9-oxa-3,7-diazabicyclo[3.3.1]nonane), or a derivative that is protected at the other nitrogen atom, with a compound of formula VII,

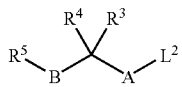

VII wherein $L^2$ represents a leaving group (e.g. mesylate, tosylate, mesitylenesulfonate or halo) and $R^3$, $R^4$, $R^5$, A and B are as hereinbefore defined, for example at between −10° C. and reflux temperature (e.g. between room temperature and reflux temperature) in the presence of a suitable base (e.g. triethylamine or an alkali metal hydrogencarbonate or carbonate, such as $K_2CO_3$) and an appropriate organic solvent (e.g. dichloromethane, acetonitrile, DMSO, chloroform, dimethylformamide, a lower (e.g. $C_{1-6}$) alkyl alcohol (such as ethanol or iso-propanol), or mixtures thereof).

Compounds of formula II in which $R^1$ represents a structural fragment of formula Ia in which A represents $C_2$ alkylene and $R^3$ and $R^4$ together represent =O may alternatively be prepared by reaction of 9-oxa-3,7-diazabicyclo[3.3.1]nonane, or a N-protected derivative thereof, with a compound of formula VIII,

VIII wherein $R^5$ and B are as hereinbefore defined, for example at room temperature in the presence of a suitable organic solvent (e.g. ethanol).

Compounds of formula II in which $R^1$ represents a structural fragment of formula Ia in which A represents $CH_2$ and $R^3$ represents —OH or —N(H)$R^7$ may alternatively be prepared by reaction of 9-oxa-3,7-diazabicyclo[3.3.1]-nonane, or a N-protected derivative thereof, with a compound of formula IX,

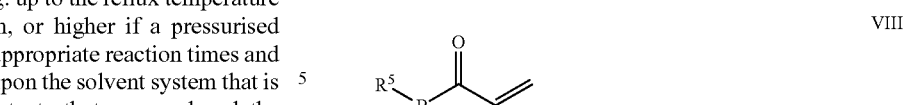

IX wherein Y represents O or N($R^7$) and $R^4$, $R^5$, $R^7$ and B are as hereinbefore defined, for example at elevated temperature (e.g. 60° C. to reflux) in the presence of a suitable solvent (e.g. a lower (e.g. $C_{1-6}$) alkyl alcohol (e.g. IPA), acetonitrile, water, toluene, a mixture of a lower (e.g. $C_{1-6}$) alkyl alcohol and water, or a mixture of a lower (e.g. $C_{1-6}$) alkyl alcohol and toluene).

Other compounds of formula II in which $R^1$ represents a structural fragment of formula Ia may alternatively be prepared by known techniques, for example according to techniques described in WO 01/28992, or by analogy with relevant processes known in the art for the introduction, and/or chemical conversion, of corresponding side-chains into, and/or in (as appropriate), corresponding bispidine compounds, for example as described in international patent application numbers WO 99/31100, WO 00/76997, WO 00/76998, WO 00/76999 and WO 00/77000, the disclosures in all of which documents are hereby incorporated by reference.

Compounds of formula III may be prepared by reaction of a corresponding compound of formula X,

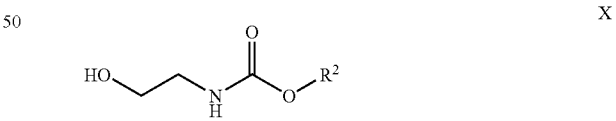

X wherein $R^2$ is as hereinbefore defined, with a compound of formula XI, $R^{16}$—S(O)$_2$-$L^3$

XI wherein $L^3$ represents a leaving group (e.g. halo, such as chloro) and $R^{16}$ is as hereinbefore defined, for example at between −20° C. (e.g. −10° C.) and room temperature in the presence of a suitable solvent (e.g. a chlorinated hydrocarbon such as dichloromethane), an appropriate base (e.g. a tertiary amine such as triethylamine) and a suitable catalyst (e.g. 4-(dimethylamino)pyridine or, preferably, a tertiary amine acid addition salt such as trimethylamine hydrochloride (see *Tetrahedron* 55, 2183 (1999)).

Compounds of formula V in which $R^1$ represents H or an amino protective group may be prepared by reaction of bis(2-oxiranylmethyl)amine (formula XII),

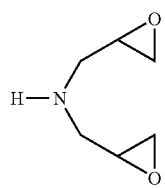                    XII or a protected (e.g. a N-benzenesulfonyl, or a N-nitrobenzenesulfonyl, such as a N-4-nitrobenzenesulfonyl) derivative thereof, with a compound of formula XIII,

  $R^{1a}$—$NH_2$                    XIII wherein $R^{1a}$ is as hereinbefore defined. This reaction may be carried out at between room temperature and the reflux temperature of any solvent that is employed (preferably at or around reflux temperature). Suitable solvent systems that may be employed include organic solvent systems, which systems should not significantly react chemically with, or significantly give rise to stereochemical changes in, the reactants or product once formed, or significantly give rise to other side reactions. Preferred solvent systems include hydroxylic compounds such as ethanol, methanol, propan-2-ol, or mixtures thereof (such as industrial methylated spirit (IMS)), optionally in the presence of an appropriate co-solvent (e.g. an ester, such as ethyl acetate, an aromatic solvent, such as toluene or chlorobenzene, or water). Preferred solvents for this reaction include primary alcohols such as methanol, propanol and, especially, ethanol, and preferred co-solvents include toluene and chlorobenzene.

Compounds of formula V in which $R^1$ represents a structural fragment of formula Ia may be prepared from the corresponding compound of formula V in which $R^1$ represents H (3,7-dihydroxy-1,5-diazacyclooctane) by known techniques (e.g. by analogy with the processes described herein in respect of the preparation of compounds of formula II). In such reactions, 3,7-dihydroxy-1,5-diazacyclooctane is optionally obtained via deprotection of a compound of formula V in which $R^1$ represents an amino protective group.

Compounds of formula VI may be prepared by known techniques, for example according to or by analogy with the procedures described in *Chem. Ber.* 96(11), 2827 (1963) and international patent application WO 01/28992.

Compounds of formula VII may be prepared by standard techniques. For example, compounds of formula VII in which:

(1) B represents -Z-O— may be prepared by coupling a compound of formula XIV,

 $R^5$—OH                    XIV wherein $R^5$ is as hereinbefore defined, to a compound of formula XV,

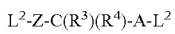 $L^2$-Z-C($R^3$)($R^4$)-A-$L^2$                    XV wherein $R^3$, $R^4$, A, Z and $L^2$ are as hereinbefore defined, and the two $L^2$ groups may be the same or different; or (2) B represents —N($R^{12}$)-Z- (wherein N($R^{12}$) is attached to the carbon atom bearing $R^3$ and $R^4$) and $R^3$ and $R^4$ together represent =O may be prepared by coupling a compound of formula XVI

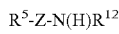 $R^5$-Z-N(H)$R^{12}$                    XVI wherein $R^5$, $R^{12}$ and Z are as hereinbefore defined, to a compound of formula XVII,

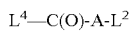 $L^4$—C(O)-A-$L^2$                    XVII wherein $L^4$ represents a suitable leaving group (e.g. —OH or halo) and A and $L^2$ are as hereinbefore defined, in both cases, under conditions which are well known to those skilled in the art.

Compounds of formula VII in which A represents $C_2$ alkylene and $R^3$ represents —$OR^6$, in which $R^6$ represents $C_{1-6}$ alkyl, -E-aryl or -E-$Het^1$ may alternatively be prepared by reaction of a compound of formula XVIII,

 $R^{6a}$—OH                    XVIII wherein $R^{6a}$ represents $C_{1-6}$ alkyl, -E-aryl or -E-$Het^1$, and E and $Het^1$ are as hereinbefore defined, with a compound of formula XIX,

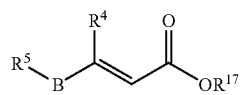                    XIX wherein $R^{17}$ represents $C_{1-4}$ alkyl, and $R^4$, $R^5$ and B are as hereinbefore defined, for example at between ambient temperature (e.g. 25° C.) and reflux temperature in the presence of a suitable base (e.g. potassium carbonate) and an appropriate organic solvent (e.g. acetonitrile), followed by conversion of the ester functionality to a —$CH_2$-$L^2$ group (in which $L^2$ is as hereinbefore defined), under conditions that are well known to those skilled in the art.

Compounds of formula VII in which A represents $C_{2-6}$ alkylene may be prepared by reduction of a corresponding compound of formula XX,

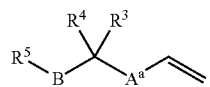                    XX wherein $A^a$ represents a direct bond or $C_{1-4}$ alkylene, and $R^3$, $R^4$, $R^5$ and B are as hereinbefore defined, with a suitable borane or borane-Lewis base complex (e.g. borane-dimethyl sulfide) in the presence of an appropriate solvent (e.g. diethyl ether, THF, or a mixture thereof), followed by oxidation of the resulting borane adduct with a suitable oxidising agent (e.g. sodium perborate) and then conversion of the resulting OH group to an $L^2$ group under conditions known to those skilled in the art.

Compounds of formula VII in which A represents $C_{1-6}$ alkylene and B represents -Z-N($R^{12}$)— (in which latter case Z is attached to the carbon atom bearing $R^3$ and $R^4$) may be prepared by coupling a compound of formula XXI,

 $R^5$-$L^5$                    XXI wherein $L^5$ represents a leaving group such as halo, alkanesulfonate, perfluoroalkanesulfonate or arenesulfonate and $R^5$ is as hereinbefore defined, with a compound of formula XXII, HN($R^{12}$)-Z-C($R^3$)($R^4$)$A^b$-OH    XXII wherein $A^b$ represents $C_{1-6}$ alkylene, Z, $R^3$, $R^4$ and $R^{12}$ are as hereinbefore defined, for example at between room and reflux temperature, optionally in the presence of a suitable solvent and/or an appropriate base, followed by conversion of the OH group to an $L^2$ group under conditions known to those skilled in the art.

Compounds of formula VII in which B represents -Z-S(O)— or -Z-S(O)$_2$— may be prepared by oxidation of corresponding compounds of formula VII in which B represents -Z-S—, wherein Z is as hereinbefore defined, in the presence of an appropriate amount of a suitable oxidising agent (e.g. mCPBA) and an appropriate organic solvent.

Compounds of formula IX may be prepared in accordance with techniques that are known to those skilled in the art. For example, compounds of formula IX in which:

(1) B represents —CH$_2$O— and Y represents O may be prepared by reaction of a compound of formula XIV, as hereinbefore defined, with a compound of formula XXIII

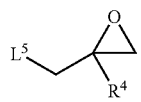

XXIII wherein $R^4$ and $L^5$ are as hereinbefore defined, for example at elevated temperature (e.g. between 60° C. and reflux temperature) in the presence of a suitable base (e.g. potassium carbonate or NaOH) and an appropriate organic solvent (e.g. acetonitrile or toluene/water), or as otherwise described in the art;

(2) $R^4$ represents H, B represents a direct bond, $C_{1-4}$ alkylene, -Z-N($R^{12}$)—, -Z-S(O)$_n$— or -Z-O— (in which, in each case, the group Z represents $C_{1-4}$ alkylene attached to the carbon atom bearing $R^4$) and Y represents O may be prepared by reduction of a compound of formula XXIVA or XXIVB,

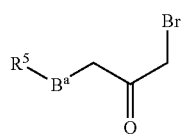

XXIVA

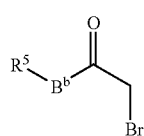

XXIVB wherein $B^a$ represents -$Z^a$-N($R^{12}$), -$Z^a$-S(O)$_n$— or -$Z^a$-O— (in which, in each case, the group $Z^a$ represents a direct bond or $C_{1-3}$ alkylene attached to the carbon atom bearing $R^4$), $B^b$ represents a direct bond or $C_{1-4}$ alkylene, and $R^5$, $R^{12}$ and n are as hereinbefore defined, for example at between −15° C. and room temperature in the presence of a suitable reducing agent (e.g. NaBH$_4$) and an appropriate organic solvent (e.g. THF), followed by an internal displacement reaction in the resultant intermediate, for example at room temperature in the presence of a suitable base (e.g. potassium carbonate) and an appropriate organic solvent (e.g. acetonitrile);

(3) B represents a direct bond, $C_{1-4}$ alkylene, -Z-N($R^{12}$)—, -Z-S(O)$_2$— or -Z-O— (in which, in each case, the group Z represents $C_{1-4}$ alkylene attached to the carbon atom bearing $R^4$) and Y represents O may be prepared by oxidation of a compound of formula XXVA or XXVB,

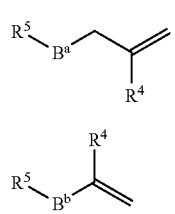

XXVA

XXVB wherein $R^4$, $R^5$ and $B^b$ are as hereinbefore defined, and $B^a$ is as hereinbefore defined except that n represents 2, in the presence of a suitable oxidising agent (e.g. mCPBA), for example by refluxing in the presence of a suitable organic solvent (e.g. dichloromethane); or (4) B represents -Z-O—, in which group Z represents $C_{1-4}$ alkylene attached to the carbon atom bearing $R^4$, and $Y^{9b}$ represents —N($R^7$), wherein $R^7$ represents —C(O)O$R^{9b}$ or —S(O)$_2R^{9c}$, may be prepared by cyclisation of a compound of formula XXVI,

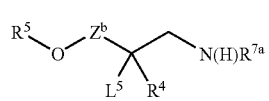

XXVI wherein $R^{7a}$ represents —C(O)O$R^{9b}$ or —S(O)$_2R^{9c}$, $Z^b$ represents $C_{1-4}$ alkylene and $R^4$, $R^5$, $R^{9b}$, $R^{9c}$ and $L^5$ are as hereinbefore defined, for example at between 0° C. and reflux temperature in the presence of a suitable base (e.g. sodium hydroxide), an appropriate solvent (e.g. dichloromethane, water, or a mixture thereof) and, if necessary, a phase transfer catalyst (such as tetrabutylammonium hydrogensulfate).

Bis(2-oxiranylmethyl)amine (the compound of formula XII) may be prepared by reaction of two or more equivalents of a compound of formula XXVII,

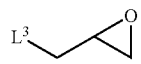

XXVII wherein $L^3$ is as hereinbefore defined, with ammonia, or a protected (e.g. a benzenesulfonyl, or a nitrobenzenesulfonyl (e.g. a 4-nitrobenzenesulfonyl)) derivative thereof, for example at between room and reflux temperature in the presence of a suitable base (e.g. an alkali metal carbonate such as cesium carbonate, sodium hydroxide, sodium hydride or lithium diisopropylamide), an appropriate solvent (e.g. acetonitrile, N,N-dimethylformamide, THF, toluene, water or mixtures thereof), and optionally in the presence of a phase transfer catalyst (e.g. tricaprylylmethylammonium chloride). Preferred bases include sodium hydroxide and preferred solvents include water.

Compounds of formula XX in which B represents $C_{1-4}$ alkylene may be prepared by coupling a compound of formula XXVIII,

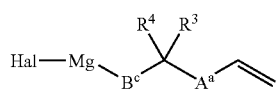
XXVIII wherein $B^c$ represents $C_{1-4}$ alkylene, Hal represents chloro, bromo or iodo, and $A^a$, $R^3$ and $R^4$ are as hereinbefore defined, with a compound of formula XXI, as hereinbefore defined, for example at between $-25°$ C. and room temperature in the presence of a suitable zinc(II) salt (e.g. anhydrous $ZnBr_2$), an appropriate catalyst (e.g. $Pd(PPh_3)_4$ or $Ni(PPh_3)_4$) and a reaction-inert organic solvent (e.g. THF, toluene or diethyl ether).

Compounds of formulae VIII, X, XI, XIII, XIV, XV, XVI, XVII, XVIII, XIX, XXI, XXII, XXIII, XXIVA, XXIVB, XXVA, XXVB, XXVI, XXVII and XXVIII, and derivatives thereof, are either commercially available, are known in the literature or may be obtained by analogy with the processes described herein, or by conventional synthetic procedures, in accordance with standard techniques, from readily available starting materials using appropriate reagents and reaction conditions.

As stated above, the process of the invention is preferably carried out to produce compounds of formula I in which $R^1$ represents an amino protective group, such as benzyl.

A preferred synthesis of compounds of formula I, however, involves synthesis of compounds of formula I in which $R^1$ represents a structural fragment of formula Ia, as hereinbefore defined, which process comprises the formation of a compound of formula I in which $R^1$ represents H or, preferably, an amino protective group (which should subsequently be removed to form a compound of formula I in which $R^1$ is H) and subsequent coupling of the resultant "intermediate" compound of formula I with a compound that provides the structural fragment of formula Ia, for example as described herein.

Thus, according five further aspects of the invention there is provided:

(I) a process for the preparation of a compound of formula I in which $R^1$ represents H, which process comprises removal of the amino protective group from a corresponding compound of formula I in which $R^1$ represents an amino protective group;

(II) a process for the preparation of a compound of formula I in which $R^1$ represents H, which process comprises a process as described hereinbefore for the preparation of a corresponding compound of formula I in which $R^1$ represents an amino protective group followed by removal of the amino protective group;

(III) a process for the preparation of a compound of formula I in which $R^1$ represents
  a) a structural fragment of formula Ia,
  b) a structural fragment of formula Ia, in which A represents $C_2$ alkylene and $R^3$ and $R^4$ together represent =O, or
  c) a structural fragment of formula Ia, in which A represents $CH_2$ and $R^3$ represents —OH or —N(H)$R^7$, which process comprises reaction of a corresponding compound of formula I in which $R^1$ represents H with
  1) a compound of formula VII, as hereinbefore defined,
  2) a compound of formula VIII, as hereinbefore defined, or
  3) a compound of formula IX, as hereinbefore defined, respectively;

(IV) a process for the preparation of a compound of formula I in which $R^1$ represents
  a) a structural fragment of formula Ia,
  b) a structural fragment of formula Ia, in which A represents $C_2$ alkylene and $R^3$ and $R^4$ together represent =O, or
  c) a structural fragment of formula Ia, in which A represents $CH_2$ and $R^3$ represents —OH or —N(H)$R^7$, which process comprises a process for the preparation of a corresponding compound of formula I in which $R^1$ represents H, as described hereinbefore, followed by reaction of that compound with
  1) a compound of formula VII, as hereinbefore defined,
  2) a compound of formula VIII, as hereinbefore defined, or
  3) a compound of formula IX, as hereinbefore defined, respectively; and (V) a process for the preparation of a compound of formula I in which $R^1$ represents
  a) a structural fragment of formula Ia,
  b) a structural fragment of formula Ia, in which A represents $C_2$ alkylene and $R^3$ and $R^4$ together represent =O, or
  c) a structural fragment of formula Ia, in which A represents $CH_2$ and $R^3$ represents —OH or —N(H)$R^7$, which process comprises a process as described hereinbefore for the preparation of a corresponding compound of formula I in which $R^1$ represents an amino protective group, removal of the amino protective group and subsequent coupling of the resulting compound of formula I in which $R^1$ represents H, with
  1) a compound of formula VII, as hereinbefore defined,
  2) a compound of formula VIII, as hereinbefore defined, or
  3) a compound of formula IX, as hereinbefore defined, respectively.

In these further aspects of the invention, amino protective groups may be removed under standard conditions. For example, when the amino protective group is benzyl, deprotection may be carried out by hydrogenation at ambient temperature in the presence of a suitable catalyst (e.g. a supported palladium catalyst, such as Pd/C, e.g. 5% (w/w) Pd/C), an appropriate solvent (e.g. a lower (e.g. $C_{1-6}$) alkyl alcohol, such as ethanol, or an aromatic hydrocarbon, such as toluene, or mixtures thereof) and optionally in the presence of a suitable base (e.g. an alkali metal carbonate or hydrogencarbonate, such as sodium hydrogencarbonate). Deprotection may also be carried out in the presence of a suitable acid. Strong acids (e.g. HCl) may be used, though we prefer that the acid is a weaker acid, such as citric acid and the like.

Further, coupling between a compound of formula I in which $R^1$ represents H and a compound of formula VII, VIII or IX may take place under any of the is relevant conditions described hereinbefore in respect of respective preparations of corresponding compounds of formula II.

In particular, where coupling takes place between a compound of formula I in which $R^1$ represents H and a compound of formula VII, then the coupling is preferably carried out at between 65 and 75° C. (such as at 70° C.) in the presence of a $C_{1-6}$ alkyl alcohol (such as ethanol) as solvent and an alkali metal carbonate (such as $K_2CO_3$) base.

Further, where coupling takes place between a compound of formula I in which $R^1$ represents H and a compound of formula IX, then the coupling is preferably carried out at between 50 and 80° C. (such as at between 60 and 75° C., such as 70° C. (e.g. 66° C. or 70° C.)) in the presence of a $C_{1-6}$ alkyl alcohol (such as iso-propanol or ethanol), water and/or toluene as solvent, and optionally in the presence of a suitable base (e.g. NaOH). Preferred solvents for this reaction include mixtures of iso-propanol and water, and mixtures of ethanol, water and toluene.

In addition to the further aspects of the invention described above, the skilled person will appreciate that certain compounds of formula I may be prepared from certain other compounds of formula I or from structurally related compounds. For example, compounds of formula I in which $R^1$ represents certain structural fragments of formula Ia may be prepared in accordance with relevant processes known in the art for the interconversion of corresponding structural fragments of formula Ia, for example by analogy with the processes described in international patent application numbers WO 99/31100, WO 00/76997, WO 00/76998, WO 00/76999, WO 00/77000 and WO 01/28992.

It will be appreciated by those skilled in the art that, in the processes described above, the functional groups of intermediate compounds may be, or may need to be, protected by protecting groups. In particular, it may be desirable to protect the amino group of bis(2-oxiranylmethyl)amine (the compound of formula XII) with an appropriate protecting group (e.g. benzenesulfonyl, nitrobenzenesulfonyl (such as 4-nitrobenzenesulfonyl)), which should be removed after the compound of formula II is formed.

In any event, functional groups which it is desirable to protect include hydroxy and amino. Suitable protecting groups for hydroxy include trialkylsilyl and diarylalkylsilyl groups (e.g. tert-butyldimethylsilyl, tert-butyldiphenylsilyl or trimethylsilyl), tetrahydropyranyl and alkylcarbonyl groups (e.g. methyl- and ethylcarbonyl groups). Suitable protecting groups for amino include the amino protective groups mentioned hereinbefore, such as benzyl, sulfonyl (e.g. benzenesulfonyl or 4-nitrobenzenesulfonyl), tert-butyloxycarbonyl, 9-fluorenylmethoxycarbonyl or benzyloxycarbonyl.

The protection and deprotection of functional groups may take place before or after any of the reaction steps described hereinbefore.

Protecting groups may be removed in accordance with techniques which are well known to those skilled in the art and as described hereinafter.

The use of protecting groups is fully described in "Protective Groups in Organic Chemistry", edited by J. W. F. McOmie, Plenum Press (1973), and "Protective Groups in Organic Synthesis", 3$^{rd}$ edition, T. W. Greene & P. G. M. Wutz, Wiley-Interscience (1999).

The process of the invention possesses the surprising advantage that compounds of formula I may be prepared conveniently from solid (as opposed to, for example, oily or semi-solid) precursors, which precursors may be purified using simple procedures (e.g. recrystallisation).

Further, the process of the invention may have the advantage that compounds of formula I may be prepared in higher yields, by way of fewer steps, in less time, more conveniently, and at a lower cost, than when prepared according to the process described in international patent application WO 01/28992.

The invention is illustrated, but in no way limited, by the following examples.

EXAMPLES

General Experimental Procedures

Mass spectra were recorded on one of the following instruments: a Waters ZMD single quad with electrospray (S/N mc350); a Perkin-Elmer SciX API 150ex spectrometer; a VG Quattro II triple quadrupole; a VG Platform II single quadrupole; or a Micromass Platform LCZ single quadrupole mass spectrometer (the latter three instruments were equipped with a pneumatically assisted electrospray interface (LC-MS)). $^1$H NMR and $^{13}$C NMR measurements were performed on Varian 300, 400 and 500 spectrometers, operating at $^1$H frequencies of 300, 400 and 500 MHz respectively, and at $^{13}$C frequencies of 75.5, 100.6 and 125.7 MHz respectively.

Rotamers may or may not be denoted in spectra depending upon ease of interpretation of spectra. Unless otherwise stated, chemical shifts are given in ppm with the solvent as internal standard.

Preparation A 2-(tert-Butyloxycarbonylamino)ethyl tosylate

A solution of p-toluenesulfonyl chloride (28.40 g, 148 mmol) in dichloromethane (100 mL) was added dropwise over 30 minutes at 0° C. to a mixture of tert-butyl N-(2-hydroxyethyl)carbamate (20 g, 120 mmol), triethylamine (18.80 g, 186 mmol) and trimethylammonium chloride (1.18 g, 12.4 mmol) in dichloromethane (120 mL). The mixture was stirred at 0° C. for 1 hour then filtered, washing with dichloromethane (100 mL). The filtrate was washed with 10% citric acid (3×100 mL) and brine (100 mL). The organic layer was dried with magnesium sulfate and then filtered. The filtrate was concentrated under reduced pressure to give an oil. The oil was dissolved in ethyl acetate (40 mL) and then iso-hexane (160 mL) was added slowly. The resultant slurry was stirred at room temperature for 17 hours and then filtered. The collected solid was washed with iso-hexane (240 mL) to yield the title compound as a colourless powder (25 g, 64%).

m.p. 64–66° C.

$^1$H-NMR (300 MHz, CDCl$_3$,) δ 1.40 (9H, s), 2.45 (3H, s), 3.38 (2H, q), 4.07 (2H, t), 4.83 (1H, bs) 7.34 (2H, d), 7.87 (2H, d).

MS: m/z=216 (MH$^+$(316)-Boc).

Preparation B

3-Benzyl-9-oxa-3,7-diazabicyclo[3.3.1]nonane (i) N,N-Bis(2-oxiranylmethyl)benzenesulfonamide Water (2.5 L, 10 vol.) followed by epichlorohydrin (500 mL, 4 eq.) were added to benzenesulfonamide (250 g, 1 eq.). The reactants were heated to 40° C. Aqueous sodium hydroxide (130 g in 275 mL of water) was added such that the temperature of the reaction remained between 40° C. and 43° C. This took approximately 2 hours. (The rate of sodium hydroxide addition needs to be slower at the start of the addition than at the end in order to keep within the temperature range stated.) After the addition of sodium hydroxide was complete, the reaction was stirred at 40° C. for 2 hours, then at ambient temperature overnight. The excess epichlorohydrin was removed as a water azeotrope by vacuum distillation (ca. 4 kPa (40 mbar), internal temp 30° C.), until no more epichlorohydrin distilled. Dichloromethane (1 L) was added and the mixture stirred rapidly for 15 minutes. The phases were allowed to separate (this took 10 minutes although totally clear phases are obtained after standing overnight). The phases were separated and the dichloromethane solution used in the subsequent step below.

$^1$H NMR (400 MHz, CDCl$_3$): δ 2.55–2.65 (2H, m), 2.79 (2H, t, J 4.4), 3.10–3.22 (4H, m), 3.58–3.73 (2H, m), 7.50–7.56 (2H, m), 7.58–7.63 (1H, m), 7.83–7.87 (2H, m).

(ii) 5-Benzyl-3,7-dihydroxy-1-phenylsulfonyl-1,5-diazacyclooctane

IMS (2.5 L, 10 vol) was added to the dichloromethane solution from step (i) above. The solution was distilled until the internal temperature reached 70° C. Approximately 1250 mL of solvent was collected. More IMS (2.5 L, 10 vol) was added followed by benzylamine (120 mL, 0.7 eq.) in one portion (no exotherm seen), and the reaction was heated at reflux for 6 hours (no change from 2 hour sampling point). More benzylamine was added (15 mL) and the solution was heated for a further 2 hours. The IMS was distilled off (ca. 3.25 L) and toluene was added (2.5 L). More solvent was distilled (ca. 2.4 L) and then further toluene added (1 L). The head temperature was now 110° C. A further 250 mL of solvent was collected at 110° C. Theoretically, this left the product in ca. 2.4 L of toluene at 110° C. This solution was used in the next step.

$^1$H NMR (400 MHz, CDCl$_3$): δ 7.83–7.80 (4H, m, ArH), 7.63–7.51 (6H, m, ArH), 7.30–7.21 (10H, ArH), 3.89–3.80 (4H, m, CH(a)+CH(b)), 3.73 (2H, s, CH$_2$Ph(a)), 3.70 (2H, s, CH$_2$Ph(b)), 3.59 (2H, dd, CHHNSO$_2$Ar(b)), 3.54 (2H, dd, CHHNSO$_2$Ar(b)), 3.40 (2H, dd, CHHNSO$_2$Ar(b)), 3.23 (2H, dd, CHHNSO$_2$Ar(a)), 3.09–2.97 (4H, m, CHHNBn(a)+CHHNBn(b)), 2.83 (2H, dd, CHHNBn(b)), 2.71 (2H, dd, CHHNBn(a))

(Data taken from purified material comprising a 1:1 mixture of trans- (a), and cis-diol (b))

(iii) 3-Benzyl-7-(phenylsulfonyl)-9-oxa-3,7-diazabicyclo[3.3.1]-nonane

The toluene solution from the previous step (ii) above was cooled to 50° C. Anhydrous methanesulfonic acid (0.2 L) was added. This caused a temperature rise from 50° C. to 64° C. After 10 minutes, methanesulfonic acid was added (1 L) and the reaction heated to 110° C. for 5 hours. Toluene was then distilled from the reaction; 1.23 L was collected. (Note that the internal temperature should not be allowed higher than 110° C. at any stage otherwise the yield will be decreased.) The reaction was then cooled to 50° C. and a vacuum applied to remove the rest of the toluene. Heating to 110° C. and 65 kPa (650 mbar) allowed a further 0.53 L to be removed. (If the toluene can be removed at a lower temperature and pressure then that is beneficial.) The reaction was then left to cool to 30° C. and deionised water (250 mL) was added. This caused the temperature to rise from 30° C. to 45° C. More water (2.15 L) was added over a total time of 30 minutes such that the temperature was less than 54° C. The solution was cooled to 30° C. and then dichloromethane (2 L) was added. With external cooling and rapid stirring, the reaction mixture was basified by adding aqueous sodium hydroxide (10 M, 2 L) at a rate that kept the internal temperature below 38° C. This took 80 minutes. The stirring was stopped and the phases separated in 3 minutes. The layers were partitioned. IMS (2 L) was added to the dichloromethane solution and distillation started. Solvent (2.44 L) was collected until the head temperature reached 70° C. Theoretically, this left the product in 1.56 L of IMS. The solution was then allowed to cool to ambient temperature overnight with slow stirring. The solid product that precipitated was filtered and washed with IMS (0.5 L) to give a fawn-coloured product that, on drying at 50° C., in vacuum, gave 50.8 g (8.9% over 3 steps).

20.0 g of this product was dissolved in acetonitrile (100 mL) at reflux to give a pale yellow solution. After cooling to ambient temperature, the crystals that formed were collected by filtration and washed with acetonitrile (100 mL). The product was dried in vacuo at 40° C. for 1 hour to give 17.5 g (87%) of sub-title compound.

$^1$H NMR (400 MHz, CDCl$_3$): δ 7.18–7.23 (10H, m), 3.86–3.84 (2H, m), 3.67 (2H, d), 3.46 (2H, s), 2.91 (2H, d), 2.85 (2H, dd), 2.56 (2H, dd)

(iv) 3-Benzyl-9-oxa-3,7-diazabicyclo[3.3.1]nonane dihydrochloride

Concentrated hydrobromic acid (1.2 L, 3 rel. vol.) was added to solid 3-benzyl-7-(phenylsulfonyl)-9-oxa-3,7-diazabicyclo[3.3.1]nonane (400 g, see step (iii) above) and the mixture was heated to reflux under a nitrogen atmosphere. The solid dissolved in the acid at 95° C. After heating the reaction for 8 hours, HPLC analysis showed that the reaction was complete. The contents were cooled to room temperature. Toluene (1.2 L, 3 rel. vol.) was added and the mixture stirred vigorously for 15 minutes. Stirring was stopped and the phases were partitioned. The toluene phase was discarded along with a small amount of interfacial material. The acidic phase was returned to the original reaction vessel and sodium hydroxide (10 M, 1.4 L, 3.5 rel. vol.) was added in one portion. The internal temperature rose from 30° C. to 80° C. The pH was checked to ensure it was >14. Toluene (1.6 L, 4 rel. vol.) was added and the temperature fell from 80° C. to 60° C. After vigorous stirring for 30 minutes, the phases were partitioned. The aqueous layer was discarded along with a small amount of interfacial material. The toluene phase was returned to the original reaction vessel, and 2-propanol (4 L, 10 rel. vol.) was added. The temperature was adjusted to between 40° C. and 45° C. Concentrated hydrochloric acid (200 mL) was added over 45 minutes such that the temperature remained at between 40° C. and 45° C. A white precipitate formed. The mixture was stirred for 30 minutes and then cooled to 7° C. The product was collected by filtration, washed with 2-propanol (0.8 L, 2 rel vol.), dried by suction and then further dried in a vacuum oven at 40° C. Yield=297 g (91%).

$^1$H NMR (CD$_3$OD+4 drops D$_2$O): δ 2.70 (br d, 2H), 3.09 (d, 2H), 3.47 (br s, 4H), 3.60 (s, 2H), 4.12 (br s, 2H), 7.30–7.45 (m, 5H).

API MS: m/z=219 [C$_{13}$H$_{18}$N$_2$O+H]$^+$.

(v) 3-Benzyl-9-oxa-3,7-diazabicyclo[3.3.1]nonane

All volumes and equivalents are measured with respect to the amount of 3-benzyl-9-oxa-3,7-diazabicyclo[3.3.1]nonane dihydrochloride (see step (iv) above) used. Toluene (420 mL, 7 vols) and aqueous sodium hydroxide solution (2M, 420 mL, 7 vols, 4.0 eq) were added to 3-benzyl-9-oxa-3,7-diazabicyclo[3.3.1]nonane dihydrochloride (60.07 g, 206.03 mmole, 1.0 eq., see step (iv) above). The mixture was stirred under nitrogen, heated to 60° C. and held at this temperature for 30 minutes by which time two clear layers had formed. The lower, aqueous layer was removed, and the toluene solution of title compound (free base) was azeodried at atmospheric pressure (total volume of solvent removed=430 mL; total volume of toluene added=430 mL), then concentrated to a volume of 240 mL (4 vols). Karl Fischer analysis at this stage showed 0.06% water in the solution. The dried solution of title compound (theoretically 44.98 g, 206.03 mmole, 1:0 eq) was used as such in a subsequent step.

Preparation C 3-(4-Cyanoanilino)propyl 4-methylbenzenesulfonate

Alternative I (i) 4-[(3-Hydroxypropyl)amino]benzonitrile

A mixture of 4-fluorobenzonitrile (12.0 g, 99.1 mmol) and 3-amino-1-propanol (59.6 g, 793 mmol) was stirred at 80° C. under an inert atmosphere for 3 hours before water (150 mL) was added. The mixture was allowed to cool to rt, and was then extracted with diethyl ether. The organic layer was separated, dried ($Na_2SO_4$), filtered and concentrated in vacuo to yield 17 g (97%) of the sub-title compound as an oil that crystallised upon standing.

(ii) 3-(4-Cyanoanilino)propyl 4-methylbenzenesulfonate

A cooled (0° C.) solution of 4-[(3-hydroxypropyl)amino]benzonitrile (from step (i) above; 17 g, 96.5 mmol) in dry MeCN (195 mL) was treated with triethylamine (9.8 g, 96.5 mmol) and then p-toluenesulfonyl chloride (20.2 g, 106 mmol). The mixture was stirred at 0° C. for 90 minutes before being concentrated in vacuo. Water (200 mL) was added to the residue, and the aqueous solution was extracted with DCM. The organic phase was dried ($Na_2SO_4$), filtered and concentrated in vacuo. The resulting residue was purified by crystallisation from iso-propanol to yield 24.6 g (77%) of the title compound.

Alternative II (a) 4-[(3-Hydroxypropyl)amino]benzonitrile

4-Fluorobenzonitrile (24.6 g, 0.203 mol, Aldrich 99%) was added to 3-amino-1-propanol (122.0 g, 1.625 mol, 8 equiv., Aldrich 99%) and the mixture heated to 80° C. for 5 hours, under nitrogen. The solution was allowed to cool to 22° C. and water (300 mL) was added. The cloudy solution was extracted twice with methylene chloride (300 mL and 200 mL) and the combined methylene chloride extracts were washed with water (300 mL) (Note 1).

(b) 3-(4-Cyanoanilino)propyl 4-methylbenzenesulfonate

The solution of the crude 4-[(3-hydroxypropyl)amino] benzonitrile (see step (a) above) was concentrated to a volume of 300 mL by distillation and a further 200 mL methylene chloride added and redistilled to 300 mL (Note 2). Triethylamine (20.55 g, 0.203 mol), followed by 4-(N,N-dimethylamino)pyridine (248 mg, 2.0 mmol) was added and the solution was cooled to 0° C. A solution of tosyl chloride (38.70 g, 0.203 mol) in methylene chloride (150 mL) added over ca. 30 minutes with cooling and good agitation, allowing the temperature to rise to 5° C. The reaction was stirred for 23 hours in the range 3 to 5° C. (Note 3) under nitrogen. Water (300 mL) was added and the layers vigorously agitated for 15 min. The organic solution was concentrated by distillation at 35 to 40° C. to a volume of ca. 60 to 70 mL. iso-Propanol (100 mL) was added over 5 minutes (Note 4). Distillation was continued using house vacuum to remove the last of the methylene chloride (Note 5). The crystal slurry was cooled to 0 to 5° C. over ca. 1 hour with slow agitation and held for one hour at 0–5° C. The crystals were filtered on a medium sinter and the compacted damp filter cake carefully washed with cold (0° C.) iso-propanol (80 mL). The filter cake was dried under vacuum and a stream of nitrogen overnight. Yield: 52.6 g, 78.4 mole %; HPLC: 99.64 area %.

Notes:

1. GC analysis of organic layer gave ~1.0 area % amino-propanol remaining.
2. Solution water by KF 0.07%
3. After 5 hours, triethylamine hydrochloride precipitation occurred. TLC showed very little if any further conversion of residual cyano alcohol at 20–23 hours.
4. At this stage, some granular precipitation of product occurred prior to addition of iso-propanol. Crystallization occurred rapidly upon addition of iso-propanol.
5. A further ~30 mL was removed—distillate checked by GC for absence of methylene chloride.
6. Microanalysis: found (theory): % C: 61.60 (61.67); % H: 5.41 (5.49); % N: 8.44 (8.47); % S: 9.71(9.70).

Preparation D

4-[(2S)-Oxiranylmethoxy]benzonitrile

Potassium carbonate (414 g) and (R)-(−)-epichlorohydrin (800 mL) were added to a stirred solution of p-cyanophenol (238 g) in 2.0 L MeCN and the reaction mixture was refluxed under an inert atmosphere for 2 h. The hot solution was filtered and the filtrate concentrated, giving a clear oil which was crystallised from di-iso-propyl ether giving the product in 90% yield.

Preparation E 2-(tert-Butyloxycarbonylamino)ethyl 2,4,6-trimethylbenzenesulfonate Triethylamine (65 mL, 465.3 mmole, 1.5 eq) was added in one portion to a solution of tert-butyl N-(2-hydroxyethyl) carbamate (50.11 g, 310.2 mmole, 1.0 eq.) in dichloromethane (250 mL, 5 vols). The solution was cooled to −10° C. and trimethylamine hydrochloride (14.84 g, 155.1 mmole, 0.5 eq.) was added in one portion. The resultant mixture was cooled further to −15° C., stirred for 5 minutes, then treated with a solution of mesitylenesulfonyl chloride (74.74 g, 341.2 mmole, 1.1 eq) in dichloromethane (250 mL, 5 vols), over 28 minutes such that the internal temperature remained below −10° C. Once the addition was complete a precipitate had formed and the mixture was stirred at −10° C. for a further 30 minutes. Water (400 mL, 8 vols) was added and all of the precipitate dissolved. The mixture was stirred rapidly for 5 minutes, and then the two layers were separated. A solvent swap from dichloromethane to IPA was carried out by distillation at reduced pressure. Solvent was removed (450 mL) and replaced with IPA (450 mL) (initial pressure was 450 mbar, b.p. 24° C.; final pressure was 110 mbar, b.p. 36° C.). At the end of the distillation, solvent (150 mL) was removed to bring the volume down to 350 mL (7 vols with respect to the amount of tert-butyl N-(2-hydroxyethyl)carbamate used). The solution was cooled to 25° C., then water (175 mL) was added slowly with stirring, causing the solution gradually to turn cloudy. No solid had precipitated at this stage. More water (125 mL) was added, and a solid precipitate started to form after about 75 mL had been added. The internal temperature rose from 25° C. to 31° C. The mixture was stirred slowly and cooled to 7° C. The solid was collected by filtration, washed with IPA:water (1:1, 150 mL) and dried in vacuo at 40° C. for 21 hours to give the title compound as a white crystalline solid (92.54 g, 87%).

m.p. 73.5° C.

$^1$H-NMR (300 MHz, $CDCl_3$) δ 1.42 (9H, s), 2.31 (3H, s), 2.62 (6H, s) 3.40 (2H, q), 4.01 (2H, t), 4.83 (1H, bs), 6.98 (2H, s)

Example 1

[2-(7-Benzyl-9-oxa-3,7-diazabicyclo[3.3.1]non-3-yl)ethyl] carbamic acid tert-butyl ester via nucleophilic substitution reaction Alternative I

[2-(7-Benzyl-9-oxa-3,7-diazabicyclo[3.3.1]non-3-yl)ethyl] carbamic acid tert-butyl ester A solution of 3-benzyl-9-oxa-3,7-diazabicyclo[3.3.1]nonane dihydro-chloride (see Preparation B(iv) above; 10 g, 34 mmol) in water (25 mL) was added slowly to a solution of sodium bicarbonate (10 g, 119 mmol) in water 10 mL). More water (5 mL) was added and the mixture was stirred at room temperature for 10 minutes. A solution of 2-(tert-butyloxycarbonylamino)ethyl tosylate (see Preparation A above; 11.92 g, 37 mmol) in toluene (40 mL) was added. This mixture was then heated at 65–70° C. for 7 hours before stirring at room temperature overnight. The reaction was reheated to 50° C. and the phases were separated. The aqueous layer was extracted with toluene (40 mL) at 50° C. The combined organic layers were washed with saturated sodium bicarbonate (25 mL). The solvents were evaporated under reduced pressure to yield a mixture of oil and solid (13 g, >100%). Ethyl acetate (50 mL) and citric acid (10%, 25 mL) were added to a portion of the oily solid (5 g, 138 mmol). The aqueous layer was separated and the organic layer washed again with citric acid (10%, 20 mL). The aqueous layers were combined and treated with solid sodium bicarbonate until neutral. The aqueous phase was extracted with ethyl acetate (2×50 mL), dried over magnesium sulfate and filtered. The filtrate was evaporated to dryness under reduced pressure to give the title compound as a colourless semi-solid, which solidified fully when stored in the refrigerator (4.68 g, 93%).

m.p. 58–60° C.

$^1$H-NMR (300 MHz, CDCl$_3$) δ 1.46 (9H, s), 2.38–2.57 (4H, m), 2.6–2.68 (2H, m) 2.75–2.85 (4H, m), 3.22 (2H, q), 3.26 (2H, s), 3.83 (2H, bs), 6.17 (1H, bs) 7.2–7.4 (5H, m).

MS: m/z=362 (MH$^+$).

Alternative II

[2-(7-Benzyl-9-oxa-3,7-diazabicyclo[3.3.1]non-3-yl)ethyl] carbamic acid tert-butyl ester, 2,4,6-trimethylbenzenesulfonic acid salt A warm (28° C.) solution of 2-(tert-butyloxycarbonylamino)ethyl 2,4,6-trimethylbenzenesulfonate (70.93 g, 206.03 mmole, 1.0 eq, see Preparation E above) in toluene (240 mL, 4 vols) was added to a solution of 3-benzyl-9-oxa-3,7-diazabicyclo[3.3.1]nonane (44.98 g, 206.03 mmole, 1.0 eq.) in toluene (240 mL, 4 vols) (see Preparation B above). The resultant solution was stirred rapidly under nitrogen, with heating at 68° C. for 8 hours. The reaction was left to stir at ambient temperature for 84 hours. A thick, white solid precipitate had formed in a pale yellow solution. The mixture was cooled to +9° C., and title compound was collected by filtration. The reaction vessel was washed with toluene (100 mL) and added to the filter. The filter cake was washed with toluene (150 mL). The white solid product was suction dried for 15 minutes, then dried to constant weight in vacuo at 40° C. for 23 hours. The yield of title compound obtained was 79.61 g, 141.7 mmole, 69%. The combined filtrate and washings (670 mL) were washed with aqueous sodium hydroxide solution (2M, 200 mL, 3.3 vols). The mixture was heated to 60° C., and held at this temperature for 20 minutes with rapid stirring. The two layers were then separated. The toluene solution was concentrated to 200 mL by vacuum distillation (bp 50–54° C. at 650–700 mbar; bp 46° C. at 120 mbar at the end). As the distillation progressed, the solution became cloudy due to the formation of title compound. It was assumed that 20% of the original amount of 3-benzyl-9-oxa-3,7-diazabicyclo[3.3.1]nonane remained in the filtrate, and so extra 2-(tert-butyloxycarbonylamino) ethyl 2,4,6-trimethylbenzenesulfonate (14.20 g, 41.21 mmole, 0.2 eq) was added in one portion (charged as a solid rather than as a solution in toluene). The cloudy solution was heated at 67° C. for 8 hours with rapid stirring, and then left to stir at ambient temperature for 11 hours. The mixture was cooled to +8° C., and title compound was collected by filtration. The reaction vessel was washed with more toluene (2×30 mL), and added to the filter. The white solid product was suction dried for 15 minutes, then dried to constant weight in vacuo at 40° C. for 7 hours. The yield of title compound was 23.25 g, 41.39 mmole, 20%. The combined yield of title compound (a white solid) was 102.86 g, 183.11 mmole, 89%.

m.p. 190–190.5° C.

$^1$H-NMR (300 MHz, CDCl$_3$) δ 1.43 (9H, s), 2.17 (3H, s), 2.51 (6H, s), 2.73–2.80 (2H, m), 2.90–2.94 (4H, m), 3.14–3.22 (4H, m), 3.37 (2H, bm), 3.89 (2H, bs), 4.13 (2H, bs), 6.74 (2H, s), 7.12 (1H, bt), 7.42–7.46 (5H, m)

Example 2

[2-(7-Benzyl-9-oxa-3,7-diazabicyclo[3.3.1]non-3-yl)ethyl] carbamic acid tert-butyl ester via Michael addition of acrylamide (i) 3-(7-Benzyl-9-oxa-3,7-diazabicyclo[3.3.1]non-3-yl)propionamide Triethylamine (3.60 g, 35.7 mmol) was added slowly to a solution of 3-benzyl-9-oxa-3,7-diazabicyclo[3.3.1]nonane dihydrochloride (see Preparation B(iv) above; 5 g, 17 mmol) in ethanol (50 mL). Acrylamide (1.34 g, 18 mmol) was added to this mixture, which was then heated at reflux for 7 hours. The reaction mixture was then concentrated under reduced pressure. Water (50 mL) and sodium hydroxide (1 M, 150 mL) were added to the residue and the mixture extracted with ethyl acetate (2×200 mL). The combined organic extracts were dried over magnesium sulfate, filtered and concentrated under reduced pressure to give a colourless solid. This was recrystallised from ethyl acetate (50 mL) to give the sub-title compound (3.80 g, 76%).

m.p. 157–159° C.

$^1$H-NMR (300 MHz, CDCl$_3$) δ 2.39 (2H, t), 2.42–2.61 (6H, m), 2.82–2.95 (4H, m), 3.39 (2H, s), 3.91 (2H, bs), 5.07 (1H, bs), 7.18–7.21 (2H, m), 7.25–7.39 (3H, m), 9.5 (1H, bs).

MS: m/z=290 (MH$^+$).

(ii) [2-(7-Benzyl-9-oxa-3,7-diazabicyclo[3.3.1]non-3-yl)ethyl]carbamic acid tert-butyl ester N-Bromosuccinimide (6.0 g, 33 mmol) was added in portions over 1 minute to a solution of 3-(7-benzyl-9-oxa-3,7-diazabicyclo[3.3.1]non-3-yl)propionamide (see step (i) above; 5 g, 12 mmol) in potassium tert-butoxide in tert-butanol (1 M, 81 mL) and tert-butanol (20 mL). The mixture was then heated at 60–65° C. for 30 minutes. The reaction was allowed to come to room temperature and then water (100 mL) was added. The mixture was extracted with ethyl acetate (2×50 mL). The combined organic extracts were washed with brine (50 mL), dried over magnesium sulfate, filtered (washing the filter cake with ethyl acetate (50 mL))

and then the filtrate concentrated under reduced pressure to give the title compound as a brown oil (6.5 g, >100%).

$^1$H-NMR (300 MHz, CDCl$_3$) δ 1.46 (9H, s), 2.4–2.58 (4H, m), 2.58–2.7 (2H, m) 2.75–2.91 (4H, m), 3.22 (2H, q), 3.28 (2H, s), 3.83 (2H, bs), 6.19 (1H, bs) 7.2–7.42 (5H, m).

MS: m/z=316 (MH$^+$).

Example 3

[2-(9-Oxa-3,7-diazabicyclo[3.3.1]non-3-yl)ethyl]carbamic acid tert-butyl ester

Alternative I

Sodium bicarbonate (0.058 g, 0.069 mmol) and 5% Pd/C (0.250 g, Johnson Matthey Type 440 paste) were added to a solution of [2-(7-benzyl-9-oxa-3,7-diazabicyclo[3.3.1]non-3-yl)ethyl]carbamic acid tert-butyl ester (see Example I (Alternative I) above; 1 g, 2.77 mmol) in ethanol (10 mL). The mixture was then hydrogenated at 500 kPa (5 bar) for 18 hours. The reaction mixture was filtered through Celite® and then washed with ethanol (20 mL). The solution was concentrated under reduced pressure to give an oil. This was dissolved in dichloromethane (20 mL) and washed with sodium hydroxide (1 M, 10 mL). The organic phase was separated, dried over magnesium sulfate and then filtered. The filtrate was concentrated under reduced pressure to give the title compound as a yellow solid (0.67 g, 87%).

m.p. 91–93° C.

$^1$H-NMR (300 MHz, CDCl$_3$) δ 1.46 (9H, s), 2.25 (2H, t), 2.58–2.65 (2H, m) 2.95–3.06 (4H, m), 3.2–3.38 (4H, m), 3.64 (2H, bs), 4.65 (1H, bs).

MS: m/z=272 (MH$^+$).

Alternative II

[2-(7-Benzyl-9-oxa-3,7-diazabicyclo[3.3.1]non-3-yl) ethyl]carbamic acid tert-butyl ester 2,4,6-trimethylbenzenesulfonic acid salt (320 g, 1.0 mol eq, 1.0 rel vol/wt, see Example 1 (Alternative II) above), toluene (640 mL, 2.0 vol) and aqueous sodium hydroxide (1M, 1.6 L, 5.0 vol) were stirred together for 15 minutes and the layers were then separated. The organic layer, containing [2-(7-benzyl-9-oxa-3,7-diazabicyclo[3.3.1]non-3-yl)-ethyl]carbamic acid tert-butyl ester, was diluted with ethanol (690 mL, 2.16 vol) and water (130 mL, 0.4 vol). Citric acid (32.83 g, 0.3 mol eq) and 5% Pd/C (20.8 g, 0.065 wt eq of 61% water wet catalyst, Johnson Matthey type 440 L) were added. The combined mixture was then hydrogenated under 4 bar of hydrogen pressure for 24 hours. The reaction was monitored by is TLC, using a silica plate with mobile phase X:DCM (1:1 v/v; X is chloroform:methanol:concentrated ammonia 80:18:2 v/v). Visualisation was by UV light (254 nm) and by staining with aqueous potassium permanganate. This showed the complete disappearance of starting material and the appearance of the title compound. The reaction mixture was filtered through kieselguhr and was washed with ethanol (590 mL, 1.84 vol). The resulting solution of title compound (assumed 154.85 g, 100%) was used directly in a subsequent reaction.

Alternative III

[2-(7-Benzyl-9-oxa-3,7-diazabicyclo[3.3.1]non-3-yl)-ethyl]-carbamic acid tert-butyl ester 2,4,6-trimethylbenzenesulfonic acid salt (50 g, 1.0 mol eq., 1.0 rel vol/wt, see Example 1 (Alternative II) above), toluene (100 mL, 2.0 vol) and aqueous sodium hydroxide (1M, 100 L, 2.0 vol) were stirred together for 20 minutes, then at 30° C. for 10 minutes, and the layers were then separated. The organic layer, containing [2-(7-benzyl-9-oxa-3,7-diazabicyclo[3.3.1]non-3-yl)ethyl]carbamic acid tert-butyl ester, was diluted with ethanol (100 mL, 2.0 vol.). To this was added a solution of citric acid (5.14 g, 0.3 mol eq) in water (5 mL, 0.1 vol), followed by 5% Pd/C (1.50 g, 0.03 wt eq of 61% water wet catalyst, Johnson Matthey type 440 L). The combined mixture was then hydrogenated under 4 bar of hydrogen pressure for 24 hours. The reaction was monitored by TLC, using a silica plate with mobile phase X:DCM 1:1 v/v, (X is chloroform:methanol:concentrated ammonia 80:18:2 v/v). Visualisation was by UV light (254 nm) and by staining with aqueous potassium permanganate. This showed the complete disappearance of starting material and the appearance of the title compound. The reaction mixture was basified with aqueous sodium hydroxide (10M, 8 mL, 0.9 mol eq), then filtered through kieselguhr. The filter-cake was washed with ethanol (100 mL, 2.0 vol). The resulting solution of title compound (assumed 24.15 g, 100%) was used directly in a subsequent reaction.

Example 4

(2-{7-[3-(4-Cyanoanilino)propyl]-9-oxa-3,7-diazabicyclo [3.3.1]non-3-yl}-ethyl)carbamic acid tert-butyl ester Alternative 1

3-(4-Cyanoanilino)propyl-4-methylbenzenesulfonate (see Preparation C above; 0.30 g, 0.92 mmol) and potassium carbonate (0.2 g, 1.38 mmol) were added to a solution of [2-(9-oxa-3,7-diazabicyclo[3.3.1]non-3-yl)ethyl]carbamic acid tert-butyl ester (see Example 3 (Alternative I) above; 0.250 g, 0.92 mmol) in ethanol (5 mL). The reaction mixture was heated to 70° C. for 10 hours before concentrating the mixture under reduced pressure. The residue was partitioned between ethyl acetate (20 mL) and sodium hydroxide (1 M, 10 mL). The aqueous phase was re-extracted with ethyl acetate (20 mL). The combined organic phases were concentrated under reduced pressure to give a yellow solid (0.290 g). The solid was dissolved in ethyl acetate (10 mL) and this solution washed with a solution of citric acid (0.250 g) in water (10 mL). The aqueous phase was separated, basified with sodium hydroxide (1 M, 10 mL) and extracted with ethyl acetate (2×10 mL). All organic phases were combined, dried over magnesium sulfate and then filtered (washing filtered solids with ethyl acetate (10 mL)). The filtrate was concentrated under reduced pressure to give a yellow solid (0.160 g). This was slurried in ethyl acetate (0.2 mL) and then filtered to give title compound (0.050 g, 12%).

m.p 113–115° C.

$^1$H-NMR (400 MHz, DMSO-D$_6$) δ 1.32 (9H, s), 1.7 (2H, qt), 2.20 (2H, t), 2.22–2.3 (4H, m), 2.38–3.1 (2H, m) 2.8–2.85 (4H, m), 3.05 (2H, q), 3.19 (2H, q), 3.79 (2H, bs), 6.47 (1H, t), 6.66 (2H, d), 6.69 (1H, t), 7.41 (2H, d).

MS: m/z=430 (MH$^+$).

Alternative 2

(a) 3-(4-Cyanoanilino)propyl benzenesulfonate

To the solution of 4-[(3-hydroxypropyl)amino]benzonitrile (see Preparation C above (first steps of both Alternatives); assumed 43.65 g, 247.7 mmol, 1.0 eq) in dichloromethane (360 mL total solution volume) was added, sequentially, triethylamine (52 mL, 37.60 g, 371.55 mmol, 1.5 eq) and trimethylamine hydrochloride (11.89 g, 123.85 mmol, 0.5 eq) in one portion. The yellow solution was cooled to −20° C. (using a cold plate), and treated with a solution of benzenesulfonyl chloride (32 mL, 43.74 g, 247.7 mmol, 1.0 eq) in dichloromethane (220 mL, 5 vols with respect to the cyanoalcohol) via a pressure equalising dropping funnel. The solution was added portionwise such that the internal temperature did not exceed −14° C. The addition took 25 minutes to complete. The mixture was then stirred for 35 minutes at between −15 and −10° C. Water (365 mL) was added and the temperature rose to 10° C. The mixture was cooled back to 0° C. and stirred vigorously for 15 minutes. The organic layer (volume 570 mL) was collected and distilled at atmospheric pressure to remove DCM (450 mL, pot temperature 40–42° C., still-head temperature 38–39° C.). Ethanol (250 mL) was added, and the solution was allowed to cool to below 30° C. before turning on the vacuum. More solvent was removed (40 mL was collected, pressure 5.2 kPa (52 mbar), pot and still-head temperatures were 21–23° C.), and the product gradually came out of solution. The distillation was stopped at this point, and more ethanol (50 mL) was added. The mixture was warmed (hot water bath at 50° C.) to 40° C. to dissolve all the solid, and water (90 mL) was added slowly via a dropping funnel. The solution was stirred slowly at room temperature (20° C.) overnight (15 hours), by which time some product had crystallised out. The mixture was cooled to −5° C. (ice/methanol bath) and stirred at this temperature for 20 minutes before collecting the pale yellow solid by filtration. The solid was washed with an ethanol/water mixture (42 mL EtOH, 8 mL H$_2$O), and suction dried for 30 minutes before drying to constant weight in the vacuum oven (40° C., 72 hours). The mass of crude product obtained was 47.42 g (149.9 mmol, 60%). Ethanol (160 mL, 8 vols) was added to the crude product (20.00 g, 63.22 mmol, 1.0 eq). The mixture was stirred under nitrogen and warmed to 40° C. using a hot water bath. On reaching this temperature, all of the solid had dissolved to give a clear, yellow solution. Water (60 mL, 3 vols) was added dropwise over a period of 10 minutes, whilst the internal temperature was maintained in the range 38–41° C. The water bath was removed, and the solution was allowed to cool to 25° C. over 40 minutes, by which time crystallisation had begun. The mixture was cooled to −5° C. over 10 minutes, then held at this temperature for a further 10 minutes. The pale yellow solid was collected by filtration, suction dried for 10 minutes, then dried to constant weight in a vacuum oven (40° C., 15 hours). The mass of sub-title compound obtained was 18.51 g (58.51 mmol, 93% (from the crude product)).

(b) (2-{7-[3-(4-Cyanoanilino)propyl]-9-oxa-3,7-diazabicyclo[3.3.1]non-3-yl}-ethyl)carbamic acid tert-butyl ester To the solution of [2-(9-oxa-3,7-diazabicyclo[3.3.1]non-3-yl)ethyl]carbamic acid tert-butyl ester generated in Example 3 (Alternative III) above (assumed 24.15 g, 1.0 mol eq., 1.0 wt./vol.) in a mixture of toluene (approx. 100 mL), ethanol (approx. 200 mL) and water (approx. 14 mL), was added anhydrous potassium carbonate (18.58 g, 1.5 mol eq.). Solid 3-(4-cyanoanilino)propyl-4-benzenesulfonate (28.17 g, 1.0 mol eq., see step (a) above) was added and the combined mixture was heated to 70° C. for six hours. The reaction was monitored by TLC using a silica plate with mobile phase X:DCM 1:1 v/v (in which X is chloroform:methanol:concentrated ammonia 80:18:2 v/v). Visualisation was by UV light (254 nm) and by staining with aqueous potassium permanganate. This showed the complete disappearance of starting material and the appearance of the title compound. The reaction mixture was cooled, and the solvent was concentrated in vacuo. The residue was partitioned between toluene (200 mL) and water (200 mL). The layers were separated, and the organic phase was concentrated in vacuo to afford a yellow solid (38.6 g). This was dissolved in iso-propanol (190 mL, 5.0 rel. vol.) at 60° C., and the hot solution was filtered. The filtrate was stirred, and left to cool to room temperature. A white solid crystallised. The mixture was cooled from room temperature to approximately 8° C. The product was collected by filtration and was washed with iso-propanol (50 mL, 2.0 vol.). The damp product was dried in vacuo at 40° C. to constant weight to give the title compound as a white crystalline solid (30.96 g, 81%).

m.p. 113.5° C.

$^1$H-NMR (400 MHz, CD$_3$OD) δ 1.40 (9H, s), 1.81–1.90 (2H, m), 2.35–2.54 (8H, m), 2.93 (4H, t) 3.18–3.27 (4H, m), 3.87 (2H, bs), 6.66 (2H, d), 7.39 (2H, d)

MS: m/z=(MH$^+$, 430)

Example 5 tert-Butyl 2-{7-[(2S)-3-(4-cyanophenoxy)-2-hydroxypropyl]-9-oxa-3,7-diazabicyclo[3.3.1]non-3-yl}ethylcarbamate Alternative I iso-Propanol (5 mL) and water (0.5 mL) were added to [2-(9-oxa-3,7-diaza-bicyclo[3.3.1]non-3-yl)ethyl]carbamic acid tert-butyl ester (see Example 3 (Alternative I) above; 0.43 g, 1.6 mmol) and 0.4-[(2S)-oxiranylmethoxy]benzonitrile(0.280 g, 1.6 mmol; see Preparation D above) was added. The mixture was heated at 66° C. for 19 hours (reaction was complete in 2 hours). The solvent was evaporated to dryness under reduced pressure to give the title compound as an off-white solid (0.71 g, 100%).

$^1$H-NMR (300 MHz, CDCl$_3$) δ 1.41 (9H, s), 2.3–2.75 (6H, m), 2.75–3.0 (5H, m), 3.1–3.38 (3H, m), 3.88 (2H, s), 3.95–4.19 (3H, m), 5.85 (1H, bs), 6.99 (2H, d), 7.6 (2H, d).

$^1$H-NMR (300 MHz, DMSO-D$_6$) δ 1.35 (9H, s), 2.12–2.59 (7H, m), 2.63–2.78 (1H, m), 2.78–2.9 (4H, m), 3.2 (2H, q), 3.78 (2H, m), 4–4.1 (2H, m), 4.12–4.19 (1H, m), 5.3 (1H, bs), 6.61 (1H, t), 7.15 (2H, d), 7.76 (2H, d).

MS: m/z=447 (MH$^+$)

Alternative II

The solution of [2-(9-oxa-3,7-diazabicyclo[3.3.1]non-3-yl)ethyl]carbamic acid tert-butyl ester generated in Example 3 (Alternative II) above (assumed 154.85 g, 1.0 mol eq, 1.0 wt/vol) in a mixture of toluene (approx 640 mL), ethanol (approx 1280 mL) and water (approx 130 mL), was basified with aqueous sodium hydroxide (10M, 51 mL, 0.9 mol eq.). Solid 4-[(2S)oxiranylmethoxy]benzonitrile (99.80 g, 1.0 mol eq.; see Preparation D above) was added and the combined mixture was heated to 70° C. for four hours. The reaction was monitored by TLC using a silica plate with mobile phase X:DCM 1:1 v/v (in which X is chloroform:methanol:concentrated ammonia 80:18:2 v/v). Visualisation was by UV light (254 nm) and by staining with aqueous potassium permanganate. This showed the complete disappearance of starting material and the appearance of the title compound. The reaction mixture was cooled, filtered through kieselguhr and washed through with ethanol (620 mL, 4.0 vol). This gave a solution of title compound (assumed 254.38 g, 100% th, 2.4 L, 1.0 wt/vol for reaction work up). This solution was charged into a flask that was set up for reduced pressure distillation. A graduation line was marked onto the side of this flask. Solvent (1250 mL) was removed at between 50° C. and 35° C., 320 mbar and 100 mbar. Then 4-methylpentan-2-ol (1500 mL) was added in order to reach the graduated line. Solvent (1250 mL) was removed at between 35° C. and 80° C., 220 mbar and 40 mbar. More 4-methylpentan-2-ol (1500 mL) was added in order to reach the graduated line. Solvent (1250 mL) was removed at between 62° C. and 76° C., 100 mbar and 90 mbar. The combined mixture was cooled to less than 25° C. and aqueous sodium hydroxide (2M, 1.27 L, 5.0 vol) was added. The layers were separated and the organic layer was filtered through kieselguhr to give a clear solution (1.2 L). This solution was charged into a clean flask, which was set up for reduced pressure distillation. Solvent (450 mL) was removed at between 52° C. and 55° C., 90 mbar and 35 mbar. Theoretically, the product was now left in 2 volumes of 4-methylpentan-2-ol. Di-n-butyl ether (1.27 L, 5 vol) was added and the solution was allowed to cool slowly to room temperature, which caused a precipitate to form. The mixture was cooled from room temperature to approximately 10° C. The product was collected by filtration and was washed with a pre-mixed solution of di-n-butyl ether (320 mL, 1.25 vol) and 4-methylpentan-2-ol (130 mL, 0.50 vol). The damp product was dried in vacuo at 55° C. to constant weight to give the title compound as a white solid (193.6 g, 76%).

m.p. 99–101° C.

$^1$H-NMR (300 MHz, CDCl$_3$) δ 1.41 (9H, s), 2.3–2.75 (6H, m), 2.75–3.0 (5H, m), 3.1–3.38(3H, m), 3.88 (2H, s), 3.95–4.19 (3H, m), 5.85 (1H, bs), 6.99 (2H, d), 7.6 (2H, d).

| Abbreviations | |
|---|---|
| API = | atmospheric pressure ionisation (in relation to MS) |
| br = | broad (in relation to NMR) |
| d = | doublet (in relation to NMR) |
| DCM = | dichloromethane |
| dd = | doublet of doublets (in relation to NMR) |
| DMF = | N,N-dimethylformamide |
| DMSO = | dimethylsulfoxide |
| Et = | ethyl |
| eq. = | equivalents |
| GC = | gas chromatography |
| h = | hour(s) |
| HCl = | hydrochloric acid |
| HPLC = | high performance liquid chromatography |
| IMS = | industrial methylated spirit |
| IPA = | iso-propyl alcohol |
| KF = | Karl-Fischer |
| m = | multiplet (in relation to NMR) |
| Me = | methyl |
| MeCN = | acetonitrile |
| min. = | minute(s) |
| m.p. = | melting point |
| MS = | mass spectroscopy |
| Pd/C = | palladium on carbon |
| q = | quartet (in relation to NMR) |
| rt = | room temperature |
| s = | singlet (in relation to NMR) |
| t = | triplet (in relation to NMR) |
| TLC = | thin layer chromatography |
| UV = | ultraviolet |

Prefixes n-, s-, i-, t- and tert- have their usual meanings: normal, secondary, iso, and tertiary.

The invention claimed is:

1. A process for the preparation of a compound of formula I,

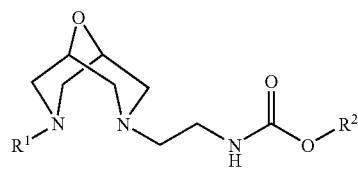

wherein $R^1$ represents H, an amino protective group or a structural fragment of formula Ia,

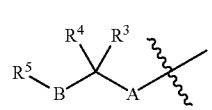

in which $R^3$ represents H, halo, $C_{1-6}$ alkyl, —OR$^6$, -E-N(R$^7$)R$^8$ or, together with $R^4$, represents =O;

$R^4$ represents H, $C_{1-6}$ alkyl or, together with $R^3$ represents =O;

$R^6$ represents H, $C_{1-6}$ alkyl, -E-aryl, -E-Het$^1$, —C(O)R$^{9a}$, —C(O)OR$^{9b}$ or —C(O)N(R$^{10a}$)R$^{10b}$;

$R^7$ represents H, $C_{1-6}$ alkyl, -E-aryl, -E-Het$^1$, —C(O)R$^{9a}$, —C(O)OR$^{9b}$, —S(O)$_2$R$^{9c}$, —[C(O)]$_p$N(R$^{10a}$)R$^{10b}$ or —C(NH)NH$_2$;

$R^8$ represents H, $C_{1-6}$ alkyl, -E-aryl or —C(O)R$^{9d}$;

$R^{9a}$ to $R^{9d}$ independently represent, at each occurrence, $C_{1-6}$ alkyl (optionally substituted and/or terminated by one or more substituents selected from halo, aryl and Het$^2$), aryl, Het$^3$, or $R^{9a}$ and $R^{9d}$ independently represent H;

$R^{10a}$ and $R^{10b}$ independently represent, at each occurrence, H or $C_{1-6}$ alkyl (optionally substituted and/or terminated by one or more substituents selected from halo, aryl and Het$^4$), aryl, Het$^5$, or together represent $C_{3-6}$ alkylene, optionally interrupted by an O atom;

E represents, at each occurrence, a direct bond or $C_{1-4}$ alkylene;

p represents 1 or 2;

A represents -G-, -J-N(R$^{11}$)— or -J-O— (in which latter two groups, N(R$^{11}$)— or O— is attached to the carbon atom bearing $R^3$ and $R^4$);

B represents -Z-,-Z-N(R$^{12}$)—, —N(R$^{12}$)-Z-, -Z-S(O)$_n$- or -Z-O—(in which latter two groups, Z is attached to the carbon atom bearing $R^3$ and $R^4$;

G represents a direct bond or $C_{1-6}$ alkylene;

J represents $C_{2-6}$ alkylene;

Z represents a direct bond or $C_{1-4}$ alkylene;

$R^{11}$ and $R^{12}$ independently represent H or $C_{1-6}$ alkyl;

n represents 0, 1 or 2;

$R^5$ represents phenyl or pyridyl, both of which groups are optionally substituted by one or more substituents selected from —OH, cyano, halo, nitro, $C_{1-6}$ alkyl (optionally terminated by —N(H)C(O)OR$^{13a}$), $C_{1-6}$ alkoxy, —N(R$^{14a}$)R$^{14b}$, —C(O)R$^{14c}$, —C(O)OR$^{14d}$, —C(O)N(R$^{14e}$)R$^{14f}$, —N(R$^{14g}$)C(O)R$^{14h}$, —N(R$^{14i}$)C(O)N(R$^{14j}$)R$^{14k}$, —N(R$^{14m}$)S(O)$_2$R$^{13b}$, —S(O)$_2$R$^{13c}$ and/or —OS(O)$_2$R$^{3d}$;

$R^{13a}$ to $R^{13d}$ independently represent $C_{1-6}$ alkyl;

$R^{14a}$ and $R^{14b}$ independently represent H, $C_{1-6}$ alkyl or together represent $C_{3-6}$ alkylene, resulting in a four- to seven-membered nitrogen-containing ring;

$R^{14c}$ to $R^{14m}$ independently represent H or $C_{1-6}$ alkyl; and

Het$^1$ to Het$^5$ independently represent, at each occurrence, five- to twelve-membered heterocyclic groups containing one or more heteroatoms selected from oxygen, nitrogen and/or sulfur, which heterocyclic groups are optionally substituted by one or more substituents selected from =O, —OH, cyano, halo, nitro, $C_{1-6}$ alkyl, $C_{1-6}$ alkoxy, aryl, aryloxy, —N(R$^{15a}$)R$^{15b}$, —C(O)R$^{15c}$, —C(O)R$^{15d}$, —C(O)N(R$^{15e}$)R$^{15f}$, —N(R$^{15g}$)C(O)R$^{15h}$ and —N(R$^{15i}$)S(O)$_2$R$^{15j}$;

$R^{15a}$ to $R^{15j}$ independently represent $C_{1-6}$ alkyl, aryl or
$R^{15a}$ to $R^{15i}$ independently represent H;
provided that:
(a) when $R^4$ represents H or $C_{1-4}$ alkyl; and
A represents -J-N($R^{11}$)— or -J-O—;
then B does not represent —N($R^{12}$)—, —S(O)$_n$—, —O— or —N($R^{12}$)-Z- (in which latter group —N($R^{12}$) is attached to the carbon atom bearing $R^3$ and $R^4$);
(b) when $R^3$ represent OR$^6$ or -E-N($R^7$)$R^8$ in which E represents a direct bond, then:
(i) A does not represent a direct bond, -J-N($R^{11}$)— or J-O—; and
(ii) B does not represent —N($R^{12}$)—, —S(O)$_n$—, —O— or —N($R^{12}$)-Z- (in which latter group —N($R^{12}$) is attached to the carbon atom bearing $R^3$ and $R^4$); and
$R^2$ represents $C_{1-6}$ alkyl (optionally substituted and/or terminated by one or more substituents selected from —OH, halo, cyano, nitro and aryl) or aryl,
wherein each aryl and aryloxy group, unless otherwise specified, is optionally substituted by one or more of —OH, cyano, halo, nitro, $C_{1-6}$ alkyl, $C_{1-6}$ alkoxy, —N($R^{14a}$)$R^{14b}$, —C(O)$R^{14c}$, —C(O)OR$^{14d}$, —C(O)N($R^{14e}$)$R^{14f}$, —N($R^{14g}$)C(O)$R^{14h}$, —N($R^{14m}$)S(O)$_2$$R^{13b}$, —S(O)$_2$$R^{13c}$ and/or —OS(O)$_2$$R^{13d}$;
which process comprises reaction of a compound of formula II,

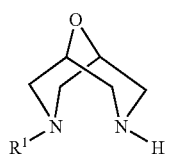

wherein as defined above, with either:
(i) a compound of formula III,

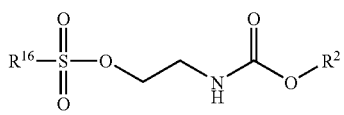

wherein $R^{16}$ represents unsubstituted $C_{1-4}$ alkyl, $C_{1-4}$ perfluoroalkyl or phenyl, which latter group is optionally substituted by one or more substituents selected from $C_{1-6}$ alkyl, halo, nitro and $C_{1-6}$ alkoxy, and $R^2$ is as defined above; or
(ii) acrylamide, followed by reaction of the resulting intermediate of formula IV,

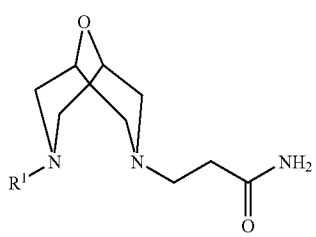

wherein $R^1$ as defined above, with an alcohol of formula $R^2$—OH and an agent that promotes, or agents that in combination promote, rearrangement and oxidation of the compound of formula IV to an intermediate isocyanate, which may then react with the alcohol of formula $R^2$—OH, wherein $R^2$ is as defined above.

2. A process as claimed in claim 1, wherein $R^2$ represents saturated $C_{1-6}$ alkyl.

3. A process as claimed in claim 2, wherein $R^2$ represents saturated $C_{3-5}$ alkyl.

4. A process as claimed in claim 3, wherein $R^2$ represents tert-butyl.

5. A process as claimed in claim 1, wherein, when $R^1$ represents an amino protective group, it represents tert-butoxycarbonyl, benzenesulfonyl or benzyl.

6. A process as claimed in claim 5, wherein $R^1$ represents benzyl.

7. A process as claimed in claim 1, wherein $R^1$ represents benzyl and $R^2$ represents tert-butyl.

8. A process as claimed in claim 1, wherein the reaction is with a compound of formula III in which $R^{16}$ represents phenyl, optionally substituted by one or more substituents selected from methyl, halo and nitro.

9. A process as claimed in claim 8, wherein $R^{16}$ represents 4-methylphenyl.

10. A process as claimed in claim 8, wherein $R^{16}$ represents 2,4,6-trimethylphenyl.

11. A process as claimed in claim 10, wherein $R^1$ represents benzyl and $R^2$ represents tert-butyl.

12. A process as claimed in claim 1, wherein the reaction is carried out in the presence of a solvent.

13. A process as claimed in claim 12, wherein the reaction is with a compound of formula III and the solvent is a $C_{1-6}$ alkyl alcohol, water, an aromatic hydrocarbon, a $C_{1-6}$ alkyl ester, or a mixture thereof.

14. A process as claimed in claim 13, wherein the solvent is water, an aromatic hydrocarbon, a $C_{1-6}$ alkyl acetate, or a mixture thereof.

15. A process as claimed in claim 14, wherein the solvent is an aromatic hydrocarbon.

16. A process as claimed in claim 14, wherein the solvent is water, toluene, iso-propyl acetate, or a mixture thereof.

17. A process as claimed in claim 16, wherein the solvent is a mixture of water and toluene.

18. A process as claimed in claim 16, wherein the solvent is toluene.

19. A process as claimed in claim 1, wherein the reaction is with a compound of formula III and is carried out at between 10 and 100° C.

20. A process as claimed in claim 19, wherein, when the solvent is a mixture of water and toluene, reaction is carried out at between 55 and 75° C.

21. A process as claimed in claim 19, wherein, when the solvent is toluene, reaction is carried out at between 60 and 70° C.

22. A process as claimed in claim 1, wherein the reaction is with a compound of formula III and the stoichiometric ratio of the compound of formula II to the compound of formula III is within the range of 3:2 to 2:3.

23. A process as claimed in claim 12, wherein reaction is with acrylamide and the solvent is DMF, N-methylpyrrolidinone, acetonitrile, DMSO, a $C_{1-6}$ alkyl alcohol, water, or a mixture thereof.

24. A process as claimed in claim 1, wherein the reaction is with acrylamide and is carried out at between 25 and 100° C.

25. A process as claimed in claim 1, wherein the reaction is with acrylamide and the stoichiometric ratio of the compound of formula II to acrylamide is within the range of 3:2 to 2:3.

26. A process as claimed in claim 1, wherein the reaction is with acrylamide and the subsequent reaction of the resulting compound of formula IV is carried out in the presence of excess $R^2$—OH.

27. A process as claimed in claim 1, wherein the reaction is with acrylamide and the subsequent reaction of the resulting compound of formula IV is carried out in the presence of a brominating agent and a base.

28. A process as claimed in claim 27, wherein the brominating agent is N-bromosuccinimide.

29. A process as claimed in claim 27, wherein the base is an alkali metal hydroxide or an alkali metal alkoxide.

30. A process as claimed in claim 29, wherein the base is potassium tert-butoxide.

31. A process as claimed in claim 27, wherein the subsequent reaction is carried out at between 25 and 100° C.

32. A process as claimed in claim 31, wherein $R^2$—OH represents tert-butanol and the reaction is carried out at between 57 and 67° C.

33. A process as claimed in claim 27, wherein the stoichiometric ratio of the compound of formula IV to the brominating agent is within the range 1:1 to 1:7.

34. A process as claimed in claim 27, wherein the stoichiometric ratio of the compound of formula IV to the base is within the range 1:1 to 1:20.

35. A process for the preparation of a compound of formula I, as defined in claim 1, in which $R^1$ represents H, which process comprises removal of the amino protective group from a corresponding compound of formula I in which $R^1$ represents an amino protective group.

36. A process as claimed in claim 35 wherein the amino protective group is benzyl.

37. A process for the preparation of a compound of formula I, as defined in claim 1, in which $R^1$ represents H, which process comprises a process, as defined in claim 1, for the preparation of a corresponding compound of formula I in which R represents an amino protective group, followed by removal of the amino protective group from that compound.

38. A process as claimed in claim 35, wherein the amino protective group is benzyl, and deprotection is carried out by hydrogenation at ambient temperature in the presence of a catalyst and a solvent.

39. A process as claimed in claim 38, wherein the catalyst is a Pd/C catalyst.

40. A process as claimed in claim 38, wherein the solvent is a $C_{1-6}$ alkyl alcohol, an aromatic hydrocarbon or a mixture thereof.

41. A process as claimed in claim 40, wherein the solvent is ethanol, toluene or a mixture thereof.

42. A process as claimed in claim 38, wherein the hydrogenation is carried out in the presence of an acid.

43. A process as claimed in claim 42, wherein the acid is a weak acid.

44. A process as claimed in claim 43, wherein the acid is citric acid.

45. A process for the preparation of a compound of formula I, as defined in claim 1, in which $R^1$ represents a structural fragment of formula Ia, which process comprises reaction of a corresponding compound of formula I in which $R^1$ represents H with a compound of formula VII,

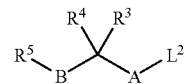

wherein $L^2$ represents a leaving group and $R^3$, $R^4$, $R^5$, A and B are as defined in claim 1.

46. A process for the preparation of a compound of formula I, as defined in claim 1, in which $R^1$ represents a structural fragment of formula Ia in which A represents $C_2$ alkylene and $R^3$ and $R^4$ together represent =O which process comprises reaction of a corresponding compound of formula I in which $R^1$ represents H with a compound of formula VIII,

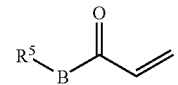

wherein $R^5$ and B are as defined in claim 1.

47. A process for the preparation of a compound of formula I, as defined in claim 1, in which $R^1$ represents a structural fragment of formula Ia in which A represents $CH_2$ and $R^3$ represents —OH or —N(H)$R^7$ which process comprises reaction of a corresponding compound of formula I in which $R^1$ represents H with a compound of formula IX,

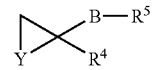

wherein Y represents O or N($R^7$) and $R^4$, $R^5$, $R^7$ and B are as defined in claim 1.

48. A process for the preparation of a compound of formula I, as defined in claim 45, which process comprises a process for the preparation of a corresponding compound of formula I in which $R^1$ represents H, followed by reaction of that compound with a compound of formula VII, as defined in claim 45.

49. A process for the preparation of a compound of formula I, as defined in claim 46, which process comprises a process for the preparation of a corresponding compound of formula I in which $R^1$ represents H, followed by reaction of that compound with a compound of formula VIII, as defined in claim 46.

50. A process for the preparation of a compound of formula I, as defined in claim 47, which process comprises a process for the preparation of a corresponding compound of formula I in which $R^1$ represents H, followed by reaction of that compound with a compound of formula IX, as defined in claim 47.

51. A process for the preparation of a compound of formula I, as defined in claim 45, which process comprises a process for the preparation of a corresponding compound of formula I in which $R^1$ represents an amino protective group, a deprotection of that compound, and subsequent coupling of the resulting compound of formula I in which $R^1$ represents H with a compound of formula VII, as defined in claim 45.

52. A process for the preparation of a compound of formula I, as defined in claim 46, which process comprises a process for the preparation of a corresponding compound of formula I in which $R^1$ represents an amino protective group, a deprotection of that compound, and subsequent coupling of the resulting compound of formula I in which $R^1$ represents H with a compound of formula VIII, as defined in claim 46.

53. A process for the preparation of a compound of formula I, as defined in claim 47, which process comprises a process for the preparation of a corresponding compound of formula I in which $R^1$ represents an amino protective group, a deprotection of that compound, and subsequent coupling of the resulting compound of formula I in which $R^1$ represents H with a compound of formula IX, as defined in claim 47.

54. A process as claimed in claim 45, wherein coupling with the compound of formula VII is carried out at between −10° C. and reflux temperature in the presence of a base and an organic solvent.

55. A process as claimed in claim 54, wherein the coupling is carried out at between 65 and 75° C.

56. A process as claimed in claim 54, wherein the solvent is a $C_{1-6}$ alkyl alcohol.

57. A process as claimed in claim 56, wherein the solvent is ethanol.

58. A process as claimed in claim 54, wherein the base is an alkali metal carbonate.

59. A process as claimed in claim 58, wherein the base is $K_2CO_3$.

60. A process as claimed in claim 47, wherein coupling with the compound of formula IX is carried out at between 60° C. and reflux in the presence of a solvent.

61. A process as claimed in claim 60, wherein the solvent is a $C_{1-6}$ alkyl alcohol, acetonitrile, a mixture of a $C_{1-6}$ alkyl alcohol and water or mixture of a $C_{1-6}$ alkyl alcohol, toluene and water.

62. A process as claimed in claim 61, wherein the alcohol is iso-propanol or ethanol.

63. A process as claimed in claim 60, wherein the reaction is carried out in the presence of a base.

64. A process as claimed in claim 63, wherein the base is sodium hydroxide.

65. A process as claimed in claim 1, wherein $R^1$ represents a structural fragment of formula Ia.

66. A process as claimed in claim 45, wherein $R^3$ represents H.

67. A process as claimed in claims 45 or 47, wherein $R^3$ represents —OH.

68. A process as claimed in claims 45 or 47, wherein $R^4$ represents H.

69. A process as claimed in claims 45 or 47, wherein A represents $CH_2$.

70. A process as claimed in any one of claims 45 to 47, wherein B represents -Z-, -Z-N(H)— or -Z-O—.

71. A process as claimed in any one of claims 45 to 47, wherein Z represents a direct bond or $C_{1-2}$ alkylene.

72. A process as claimed in any one of claims 45 to 47, wherein $R^5$ represents para-cyanophenyl.

73. A process as claimed in claims 45 or 48, wherein, in the compound of formula I that is ultimately produced, $R^1$ represents the sub-structure

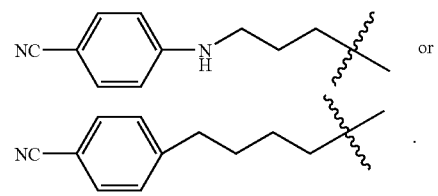

74. A process as claimed in claims 45 or 47, wherein, in the compound of formula I that is ultimately produced, $R^1$ represents the sub-structure

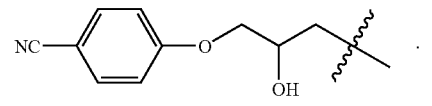

75. A process as claimed in claim 74, wherein, in the compound of formula I that is ultimately produced, $R^1$ represents the sub-structure

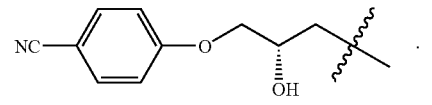

76. 2-(tert-Butyloxycarbonylamino)ethyl 2,4,6-trimethylbenzenesulfonate.

77. [2-(7-Benzyl-9-oxa-3,7-diazabicyclo[3.3.1]non-3-yl)ethyl]carbamic acid tert-butyl ester, 2,4,6-trimethylbenzenesulfonic acid salt.

* * * * *

UNITED STATES PATENT AND TRADEMARK OFFICE
CERTIFICATE OF CORRECTION

PATENT NO. : 7,169,921 B2  Page 1 of 1
APPLICATION NO. : 10/474593
DATED : January 30, 2007
INVENTOR(S) : Lal Cheema et al.

It is certified that error appears in the above-identified patent and that said Letters Patent is hereby corrected as shown below:

Column 32, Claim 1, Line 53, "and/or _OS(O)2R$^{3d}$" should read -- and/or _OS(O)2R$^{13d}$ --.

Column 35, Claim 37, Line 43, "which R represents an amino protective group, followed by" should read -- which R$^1$ represents an amino protective group, followed by --.

Signed and Sealed this

Sixteenth Day of June, 2009

JOHN DOLL
*Acting Director of the United States Patent and Trademark Office*